(12) United States Patent
Walen et al.

(10) Patent No.: US 11,660,148 B2
(45) Date of Patent: May 30, 2023

(54) SYSTEM AND METHOD FOR MONITORING OFFSET DURING NAVIGATION-ASSISTED SURGERY

(71) Applicant: Stryker Corporation, Kalamazoo, MI (US)

(72) Inventors: James G. Walen, Portage, MI (US); Zachary Bolthouse, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 279 days.

(21) Appl. No.: 17/147,599

(22) Filed: Jan. 13, 2021

(65) Prior Publication Data

US 2021/0212769 A1 Jul. 15, 2021

Related U.S. Application Data

(60) Provisional application No. 63/054,811, filed on Jul. 22, 2020, provisional application No. 62/960,218, filed on Jan. 13, 2020.

(51) Int. Cl.
*A61B 34/20* (2016.01)
*A61B 34/10* (2016.01)
(Continued)

(52) U.S. Cl.
CPC .............. *A61B 34/20* (2016.02); *A61B 17/15* (2013.01); *A61B 17/1703* (2013.01); *A61B 17/1757* (2013.01); *A61B 34/10* (2016.02); *A61B 2017/00039* (2013.01); *A61B 2017/00119* (2013.01); *A61B 2017/00123* (2013.01); *A61B 2017/00199* (2013.01);
(Continued)

(58) Field of Classification Search
CPC ......... A61B 34/20; A61B 34/10; A61B 17/15; A61B 17/17; A61B 17/1757; A61B 17/1703
See application file for complete search history.

(56) References Cited

U.S. PATENT DOCUMENTS 5,086,401 A 2/1992 Glassman et al.
5,445,166 A 8/1995 Taylor
(Continued)

FOREIGN PATENT DOCUMENTS

TW 201106916 A 3/2011
WO 2007136770 A2 11/2007
(Continued)

OTHER PUBLICATIONS

International Search Report for Application No. PCT/US2021/013206 dated Jul. 26, 2021, 3 pages.
(Continued)

*Primary Examiner* — Christopher J Beccia
(74) *Attorney, Agent, or Firm* — Howard & Howard Attorneys PLLC

(57) ABSTRACT

Surgical systems and methods for tracking physical objects near a target site during a surgical procedure are provided, the surgical system employs a navigation system and a surgical instrument; an instrument tracker is provided on the surgical instrument and a patient tracker is provided on the patient's target tissue; the system and method is configured to detect an error condition compromising accuracy of the navigation guidance and to track and monitor a tool-to-bone offset.

24 Claims, 14 Drawing Sheets

(51) Int. Cl.
*A61B 17/15* (2006.01)
*A61B 17/17* (2006.01)
*A61B 17/00* (2006.01)

(52) U.S. Cl.
CPC ............... *A61B 2017/00398* (2013.01); *A61B 2034/104* (2016.02); *A61B 2034/105* (2016.02); *A61B 2034/2051* (2016.02); *A61B 2034/2057* (2016.02); *A61B 2034/2072* (2016.02); *A61B 2217/005* (2013.01)

(56) References Cited

U.S. PATENT DOCUMENTS

| | | |
|---|---|---|
| 5,834,759 A | 11/1998 | Glossop |
| 5,987,960 A | 11/1999 | Messner et al. |
| 6,306,126 B1 | 10/2001 | Moctezuma |
| 6,674,030 B2 | 1/2004 | Chen et al. |
| 6,711,431 B2 | 3/2004 | Sarin et al. |
| 6,741,883 B2 | 5/2004 | Gildenberg |
| 6,757,582 B2 | 6/2004 | Brisson et al. |
| 6,887,245 B2 | 5/2005 | Kienzle, III et al. |
| 6,947,783 B2 | 9/2005 | Immerz |
| 6,996,487 B2 | 2/2006 | Jutras et al. |
| 7,043,961 B2 | 5/2006 | Pandey et al. |
| 7,190,331 B2 | 3/2007 | Gene et al. |
| 7,206,626 B2 | 4/2007 | Quaid, III |
| 7,289,227 B2 | 10/2007 | Smetak et al. |
| 7,346,417 B2 | 3/2008 | Luth et al. |
| 7,696,899 B2 | 4/2010 | Immerz et al. |
| 7,725,162 B2 | 5/2010 | Malackowski et al. |
| 7,831,292 B2 | 11/2010 | Quaid et al. |
| 7,831,295 B2 | 11/2010 | Friedrich et al. |
| 7,962,196 B2 | 6/2011 | Tuma |
| 8,031,922 B2 | 10/2011 | Haimerl et al. |
| 8,046,052 B2 | 10/2011 | Verard et al. |
| 8,060,181 B2 | 11/2011 | Rodriguez Ponce et al. |
| 8,165,366 B2 | 4/2012 | Haimerl et al. |
| 8,249,689 B2 | 8/2012 | Anderson |
| 8,287,522 B2 | 10/2012 | Moses et al. |
| 8,328,793 B2 | 12/2012 | Birkenbach et al. |
| 8,504,139 B2 | 8/2013 | Jacobsen et al. |
| 8,560,047 B2 | 10/2013 | Haider et al. |
| 8,652,140 B2 | 2/2014 | Neubardt et al. |
| 8,663,120 B2 | 3/2014 | Markowitz et al. |
| 8,867,809 B2 | 10/2014 | Vincent et al. |
| 8,876,830 B2 | 11/2014 | Hodorek et al. |
| 9,220,573 B2 | 12/2015 | Kendrick et al. |
| 9,232,985 B2 | 1/2016 | Jacobsen et al. |
| 9,342,632 B2 | 5/2016 | Zoran et al. |
| 9,351,782 B2 | 5/2016 | Stein et al. |
| 9,393,039 B2 | 7/2016 | Lechner et al. |
| 9,566,120 B2 | 2/2017 | Malackowski et al. |
| 9,724,165 B2 | 8/2017 | Arata et al. |
| 9,788,906 B2 | 10/2017 | Piron et al. |
| 9,814,532 B2 | 11/2017 | Bell et al. |
| 9,901,356 B2 | 2/2018 | Shen et al. |
| 9,925,017 B2 | 3/2018 | Schmidt |
| 9,993,305 B2 | 6/2018 | Andersson |
| 10,028,789 B2 | 7/2018 | Quaid et al. |
| 10,034,713 B2 | 7/2018 | Yang et al. |
| 10,080,617 B2 | 9/2018 | Haider et al. |
| 10,092,361 B2 | 10/2018 | Ferro et al. |
| 10,179,032 B2 | 1/2019 | Andersson |
| 10,198,662 B2 | 2/2019 | Vincent et al. |
| 10,390,892 B2 | 8/2019 | Witcomb et al. |
| 2004/0073279 A1 | 4/2004 | Malackowski et al. |
| 2004/0167393 A1 | 8/2004 | Solar et al. |
| 2011/0015649 A1 | 1/2011 | Anvari et al. |
| 2011/0046636 A1 | 2/2011 | Wu et al. |
| 2011/0054449 A1 | 3/2011 | Tien et al. |
| 2012/0029387 A1 | 2/2012 | Wei et al. |
| 2013/0060278 A1 | 3/2013 | Bozung et al. |
| 2016/0074123 A1 | 3/2016 | Bly et al. |
| 2016/0120609 A1 | 5/2016 | Jacobsen et al. |
| 2016/0135904 A1 | 5/2016 | Daon et al. |
| 2016/0192960 A1 | 7/2016 | Bueno et al. |
| 2016/0354162 A1 | 12/2016 | Yen et al. |
| 2017/0007327 A1 | 1/2017 | Haider et al. |
| 2017/0202624 A1 | 7/2017 | Atarot et al. |
| 2017/0245947 A1 | 8/2017 | Bozung et al. |
| 2017/0252109 A1 | 9/2017 | Yang et al. |
| 2017/0265774 A1 | 9/2017 | Johnson et al. |
| 2017/0304011 A1 | 10/2017 | Markey et al. |
| 2018/0028266 A1 | 2/2018 | Barnes et al. |
| 2018/0085172 A1 | 3/2018 | Bell et al. |
| 2018/0140223 A1 | 5/2018 | Kheradpir et al. |
| 2018/0161120 A1 | 6/2018 | Verard et al. |
| 2018/0168750 A1 | 6/2018 | Staunton et al. |
| 2018/0200001 A1 | 7/2018 | Erbe |
| 2018/0250077 A1 | 9/2018 | Xu et al. |
| 2018/0325608 A1 | 11/2018 | Kang et al. |
| 2018/0325610 A1 | 11/2018 | Cameron et al. |
| 2018/0353243 A1 | 12/2018 | Ferro et al. |
| 2019/0015164 A1 | 1/2019 | Quaid et al. |
| 2019/0029697 A1 | 1/2019 | Anderson et al. |
| 2019/0350657 A1 | 11/2019 | Tolkowsky |
| 2020/0129243 A1 | 4/2020 | Kemp et al. |
| 2020/0146758 A1 | 5/2020 | Millahn et al. |

FOREIGN PATENT DOCUMENTS

| | | |
|---|---|---|
| WO | 2008053056 A1 | 5/2008 |
| WO | 2015021216 A1 | 2/2015 |
| WO | 2017087371 A1 | 5/2017 |
| WO | 2017157763 A1 | 9/2017 |
| WO | 2018195216 A1 | 10/2018 |

OTHER PUBLICATIONS

English language abstract for TW 201106916 A extracted from espacenet.com database on Jan. 27, 2021, 2 pages.
English language abstract for WO 2008/053056 A1 and machine-assisted English translation for equivalent ES 2302450 A1 extracted from espacenet.com database on Jan. 27, 2021, 10 pages.
Partial International Search Report for Application No. PCT/US2021/013206 dated May 3, 2021, 2 pages.

SYSTEM AND METHOD FOR MONITORING OFFSET DURING NAVIGATION-ASSISTED SURGERY

REFERENCE TO RELATED APPLICATION

This application claims priority to and all the benefits of U.S. Provisional Patent Application No. 63/054,811, filed Jul. 22, 2020; and U.S. Provisional Patent Application No. 62/960,218, filed Jan. 13, 2020, the entire contents of which are hereby incorporated by reference.

BACKGROUND

The present disclosure generally relates to computer-assisted surgery. More specifically, a system and technique for calculating an offset between a monitored position of a surgical device relative to a patient is disclosed. The technique may be implemented as a method, as a computer-program non-transitory media, as a computing device, and as a system for computer assisted surgery.

Navigation-assisted surgery is often conducted based on pre-operatively imaged patient anatomy, utilizing one or more of magnetic resonance imaging (MRI), computerized tomography (CT), X-ray, or other imaging technology. Data generated through these techniques can be very accurate and provide a basis for generating a virtual three-dimensional (3D) model of the subject anatomy stored in the memory in a navigation system or in communication with the navigation system. During navigation-assisted surgery, a patient tracker can be associated with the patient's anatomy and a tool tracker can be associated with the surgical tool. The navigation system can locate and track the anatomy and the surgical tool based on the associated trackers in a virtual space of the navigation system to provide critical information to the surgeon or other medical professionals during the surgery.

Surgical navigation systems are used in industrial, aerospace, and medical applications to precisely locate and track physical objects in space and orientation. In the medical field specifically, navigation systems can assist surgeons or other medical professionals in precisely placing surgical instruments relative to a target site in a patient, for example, during a surgical operation. The target site usually requires some form of therapy or treatment, such as tissue removal. Conventional navigation systems employ a localizer, including one or more sensors that cooperate with trackers to provide position and/or orientation data associated with the surgical information and the target site, e.g., the volume of tissue requiring treatment. These trackers allow a surgeon to see the position and/or orientation of the surgical tool overlaid on a monitor in conjunction with a virtual representation of the tool and the anatomy based on preoperative or intraoperative imaging of the patient. These tracker also allow the navigation system to monitor the relative positioning of the tool and the anatomy to alert the user when the tool approaches or enters an undesirable position relative to the anatomy. For example, to alert the user that the tool is nearing or contacting patient tissue that is not intended to be contacted by the tool.

The localizer is usually placed so that it has a field of view of the trackers, that is, the localizer is positioned so that the target site of the patient is within the target space of the localizer. The trackers include identifiable arrays of fiducials or markers that are fixed to at least one of a surgical instrument or a patient to move in concert with the surgical instrument or the patient, respectively. From the detected position of the trackers, the surgical navigation system can determine the position and orientation of the surgical instrument or patient and monitor the determined position and orientation for changes over time. The term position refers to the 3D coordinate values of an object's coordinate system relative to a reference coordinate system used by the surgical navigation system. The term orientation refers to the pitch, roll and yaw of the object's coordinate system relative to the reference coordinate system. Collectively, the position and the particular pitch, roll, and yaw values of a given orientation may be referred to as the object's pose in the reference coordinate system. When both the position and orientation (or pose) are defined, the object is known to and trackable by (i.e., registered by) the surgical navigation system.

The tracker attached to the patient and the tracker attached to the tool are rigidly secured to the bone and the tool applying the treatment, thereby maintaining a fixed relationship with respect to the target site and tool owing to the rigid nature of the bone or tool, the rigid structure of the tracker, and the fixed securement therebetween. In alternatives known in the art, trackers may be deformable, affixed to flexible tissues such as skin, where the tracker comprises a pattern or arrangement of markings, markers, or fiducials, according to a known deformation that provides similar information as rigid trackers. By using separate trackers on the surgical tool and on the patient, the treatment end of the surgical instrument can be precisely positioned at the target site by the surgeon aided by the navigation system.

During an initial phase of the operation, an object, whether a surgical tool or a patient's anatomy, must be calibrated or registered to the surgical navigation system. The process of calibration or registration refers to establishing a relationship between the physical object and its tracker to virtual representations of the object and tracker as data within the surgical navigation system—that is, virtual object data and virtual tracker data, respectively. The virtual data, whether for the object or the tracker, may or may not be a model of the object. Rather, the virtual data may comprise information sufficient to identify or designate certain points of interest and may further include other information about the dimensional characteristics of the object. The virtual data may be established pre-operatively or intra-operatively. The virtual data may be based on pre-existing modeling or object specification data, or may be based on imaging of the object in situ. The virtual data may be generated from imaging data through a process of segmentation. For example, pre-operative imaging of a patient's anatomy may be used to generate a 3D model of that anatomy as virtual object data in the memory and virtual environment of the surgical navigation system. Likewise, a surgical tool may be manufactured according to known geometry and structure. This geometry and structure may be represented in a 3D model of that tool as virtual object data in the memory and virtual environment of the surgical navigation system. To perform the calibration, additional reference pointers or frames having additional tracker fiducial arrays may be required to touch off reference points according to a registration or calibration system. Alternatively, calibration may be established using optical processes, using projected light patterns, optical recognition, or other conventional methods.

The localizer is typically provided with multiple sensing technologies variously adapted for beneficial use in a particular aspect of the operation. In one example, a localizer may be provided with one or more sensors adapted for navigation. The one or more navigation sensors may be adapted for navigation by operating a high frequency of sensing cycles to accurately track small movements over small increments of time—i.e., providing a high resolution of tracking data.

The localizer may be further provided with sensors adapted for machine vision or other applications beneficial to the operation. For example, the localizer may be provided with one or more optical cameras to provide video recording of the surgical operation. The localizer may include multiple sets of discrete sensors that perform different functions, that is, sense different physical properties or light, electromagnetic energy, or other characteristics. The data representing the sensor output of the localizer may be processed to derive important information about the surgical site within the field of view or range of the localizer.

Conventional surgical navigation systems may be adapted for use with a robotic arm or manipulator supporting the surgical tool used during the medical operation. Incorporating the robotic arm manipulator with the navigation system provides a further degree of control such that movement of the surgical tool is accomplished by or with the help of the robotic arm to ensure the proper placement of the tool relative to the anatomy. Joint encoders or other sensing technology can be incorporated into the robotic arm to provide additional data to determine the location of the tool while it is being tracked with the navigation system. This information can be compared, and if a discrepancy arises, the operator can be alerted, and the surgical operation halted until the error can be diagnosed and corrected.

Improvements in surgical navigation systems adapted for use without the assistance of a robotic manipulator are needed. Excluding the closed loop of data provided by the robotic system introduces additional uncertainty, leaving open the risk that the navigation system loses calibration or registration to the tool or anatomy trackers without the ability to detect such loss of calibration or registration and without alerting the user. This can lead to the potential improper placement of the tool relative to the anatomy during the operation. Thus, there is a need in the art for systems and methods that address the shortcomings of conventional navigation systems, providing an effective technique for monitoring an offset during navigation assisted surgery.

SUMMARY

A method of navigating a surgical instrument having a variable speed motor relative to a bone is provided. The method includes using a navigation system including a localizer having a localizer coordinate system. An instrument tracker is coupled to the surgical instrument. A patient tracker is coupled to the bone. A controller is in communication with the navigation system. The controller controls the surgical instrument.

The method includes registering, with the localizer, the patient tracker in the localizer coordinate system, the registration defining the location of the bone relative to the localizer coordinate system. The method includes registering, with the localizer, the instrument tracker in the localizer coordinate system, the registration defining the location of an instrument tool tip relative to the localizer coordinate system.

The method includes defining a motor operation for the instrument when the instrument tool tip is not in contact with the bone. The method includes monitoring, with the controller, motor operation of the instrument during a medical procedure and monitoring, with the navigation system, a position of the instrument tool tip relative to the bone to determine when the instrument tool tip is in contact with the bone in the localizer coordinate system.

The method includes comparing the motor operation to the monitored position of the instrument tool tip; and determining an error condition when the monitored position of the instrument tool tip is in contact with the bone in the localizer coordinate system and the monitored motor operation equals the defined motor operation for the instrument when the instrument tool tip is not in contact with the bone. The method includes triggering an action when an error condition is determined.

In the method, the step of defining the motor operation for the instrument when the tool tip is not in contact with the bone may include defining a threshold value for power, voltage, current, or combinations thereof, when the instrument motor is operated while the instrument tool tip is not in contact with bone. The step of defining the motor operation may include storing data representing the motor operation in a memory of one or more of the controller, the navigation system, the surgical instruments, or combinations thereof.

The method may also include the step of defining a second motor operation for the instrument when the instrument tool tip is in contact with the bone. Defining a second motor operation, the method may further include determining a second error condition when the monitored position of the instrument tool tip is not in contact with the bone in the localizer coordinate system and the monitored motor operation equals the second defined motor operation for the instrument when the instrument tool tip is in contact with the bone. The method may also include triggering a second action when the second error condition is determined.

In the method, the step of triggering one of an action or a second action comprises one of sounding an audible alert, displaying a visual alert, activating a tactile alert, cutting off power to the surgical instrument, or combinations thereof.

A method of navigating a surgical instrument having a variable speed motor relative to a bone and monitoring a tool-to-bone offset is provided. The method includes using a navigation system including a localizer having a localizer coordinate system. An instrument tracker is coupled to the surgical instrument. A patient tracker is coupled to a bone. A controller is in communication with the navigation system and controls the surgical instrument.

The method includes registering, with the localizer, the patient tracker in the localizer coordinate system, the registration defining the location of the bone relative to the localizer coordinate system. The method includes registering, with the localizer, the instrument tracker in the localizer coordinate system, the registration defining the location of an instrument tool tip relative to the localizer coordinate system.

The method includes defining a first motor operation of the surgical instrument operating while not in contact with the bone. The method includes monitoring, with the controller, a motor operation of the surgical instrument during a medical procedure; and monitoring, with the navigation system, a position of the instrument tool tip relative to the bone in the localizer coordinate system.

The method includes comparing the monitored motor operation to the defined motor operation; and determining a contact time between the instrument tool tip and the bone when the monitored motor operation deviates from the defined first motor operation. The method includes determining, with the navigation system at the contact time, a tool-to-bone offset as a distance between the instrument tool tip and a surface of the bone in the localizer coordinate system. Although described herein as a tool-to-bone offset, it should be appreciated that the reference to "bone" is not intended to be limiting, and the use of "bone" in this way can be understood as any type anatomical structure upon which a surgical operation is performed and includes non-bone type tissues, such as skin, muscle, connective tissues, nervous tissues, and others. The method includes triggering an action when the tool-to-bone offset exceeds a predefined magnitude.

In the method, the step of triggering an action may include one of sounding an audible alert, displaying a visual alert, activating a tactile alert, cutting off power to the surgical instrument, or combinations thereof. In the method, the predefined magnitude may be equal to 0.5 millimeters. The step of triggering an action may include prompting a user to update a model of the bone, and the method may include the step of updating the model of the bone. The step of updating the model includes contacting a resected surface of the bone with the instrument tool tip while power is disabled from the controller to the surgical implement.

The method may further include displaying, on a display device, the determined tool-to-bone offset. The method may include displaying the series of tool-to-bone offsets as a chart of offset values over time.

In the method, the step of monitoring the position of the instrument tool tip relative to the bone may include tracking the location of the instrument tool tip and the location of the bone during the medical procedure; and may further include detecting, with the navigation system, each occurrence during the operation of the monitored location of the instrument tool tip being in contact with the surface of the bone and logging a series of tool-to-bone offset values determined in the course of the medical procedure upon each occurrence. The method may further include displaying, on a display device, the series of tool-to-bone offsets as a continuously updating value.

The method may further include defining a first level magnitude and a second level magnitude. In the method the step of displaying the determined tool-to-bone offset may include displaying the offset in a first color when the offset is less than the first level magnitude, displaying the offset in a second color, different from the first color, when the offset is between the first level and the second level magnitude; and displaying the offset in a third color, different from the first and the second colors, when the offset is greater than the second level magnitude. The predefined magnitude for triggering an action may be equal to the second level magnitude. The predefined magnitude for triggering an action may be greater than the second level magnitude. The method may further include defining a third level magnitude, wherein the method also includes disabling power from the controller to the surgical instrument when the tool-to-bone offset is greater than the third level magnitude. The method may include prompting a user to enter a value for the predefined magnitude, the first level magnitude, the second level magnitude, the third level magnitude, or combinations thereof. The method may include disabling power from the controller to the surgical instrument when the tool-to-bone offset is greater than the predefined value.

A surgical system is provided. The surgical system includes a surgical instrument having a variable speed motor, or actuator, and a tool tip. The surgical system includes a controller for providing power to the surgical instrument, the controller operable to monitor a motor, or actuator, operation of the instrument, the controller comprising a processor and a memory, the memory operable to store information, including information representing the operation of the instrument. The system includes an instrument tracker coupled to the instrument and a patient tracker to be coupled to a bone.

The system includes a navigation system comprising a localizer. The navigation system is operable to store information representing the surgical instrument, and information representing the bone, in a virtual space. The navigation system is operable to track the location of the instrument and the bone in the virtual space during the operation based on information gathered by the localizer. The localizer is operable to register a location of the instrument tracker and a location of the patient tracker relative to a localizer coordinate system, and to gather information about the location of the instrument and the bone in cooperation with the instrument tracker and the patient tracker, respectively. The controller and the navigation system are in electronic communication and configured to cooperate. The controller and the navigation system determine, based on a change in the operation, a time of contact between the tool tip and the bone. The controller and the navigation system determine, at the time of contact, a tool-to-bone offset as a distance between the tracked location of the tool tip and the tracked location of the bone. The system also includes an alert device, wherein the controller and the navigation system are further configured to trigger an action when the tool-to-bone offset is greater than a predefined magnitude.

A method of operating a surgical navigation system during a surgical operation to verify a tracking registration is provided. The surgical navigation system includes a localizer having a localizer coordinate system. An instrument tracker is coupled to a surgical instrument. The surgical instrument includes a tool tip. A patient tracker is coupled to a patient's anatomy. A control console communicates with the localizer. The control console communicates with data representing the surgical instrument and data representing the patient's anatomy.

The method includes tracking the surgical instrument and the anatomy with the navigation system and storing first data representing the tracked surgical instrument and second data representing the tracked anatomy in a common coordinate system with the control console. The method includes determining the tool tip is within a predefined proximity to the tracked anatomy based on the tracked surgical instrument and the tracked anatomy. The method includes determining the tool tip does not depart the predefined proximity by more than a predefined magnitude over a predefined duration. The method includes determining an offset distance based on the first data representing the tracked surgical instrument and the second data representing the tracked anatomy. The method includes comparing the offset distance to a predefined threshold; and triggering an action of the navigation system when the offset distance is greater than the predefined threshold.

Optionally, the method includes prompting a user to verify a tracking registration by one of displaying a prompt on a display; sounding an audible alert; generating a haptic sensation; or combinations thereof.

In the method, the step of determining that the tool tip is within a predefined proximity to the anatomy may include defining a surface area of the anatomy not to be resected and determining the tool tip is within a predefined proximity to the defined surface area.

In the method, the offset distance may be defined as a magnitude of minimum separation between the tool tip and the tracked anatomy in the common coordinate system, or as a magnitude of greatest overlap between the tool tip and the tracked anatomy in the common coordinate system.

In the method, determining the tool tip is within a predefined proximity to the tracked anatomy may include the surgical instrument positioned at a first pose with respect to the tracked anatomy, and the surgical instrument may define a first proximal point of the tool tip and determining the offset distance may include determining a first offset distance. The method further includes determining that the tool tip is within a predefined proximity to the tracked anatomy and includes the surgical instrument positioned at a second pose with respect to the tracked anatomy, where the surgical instrument may define a second proximal point of the tool tip and where determining the offset distance may include determining a second offset distance.

The step of comparing the offset distance to a predefined threshold may include comparing the first offset distance to the predefined threshold and comparing the second offset distance to the predefined threshold. The step of initiating an action therefore may include initiating an action when the first offset distance, the second offset distance, or both the first and second offset distances are greater than the predefined threshold.

The surgical instrument may include an elongated aspect terminating at the tool tip, the elongated aspect defining a longitudinal axis extending substantially parallel to the elongated aspect; and wherein the second proximal point is at least 90° from the first proximal point relative to a rotation about the centerline. The surgical instrument may include the tool tip having a spherical aspect defining a centerpoint, wherein the second proximal point is at least 90° away from the first proximal point relative to a rotation about the centerpoint.

The step of determining that the tool tip is within a predefined proximity to the tracked anatomy may include the surgical instrument being positioned at a third pose with respect to the tracked anatomy. The surgical instrument may define a third proximal point, the third proximal point being different from the first proximal point and different from the second proximal point. The step of determining the offset distance may include determining a third offset distance.

The step of comparing the offset distance to a predefined threshold may include comparing the first offset distance to the predefined threshold, comparing the second offset distance to the predefined threshold, and comparing the third offset distance to the predefined threshold. The step of initiating an action may include initiating an action when the first offset distance, the second offset distance, the third offset distance or combinations thereof are greater than the predefined threshold.

The step of triggering an action may include one of sounding an audible alert, displaying a visual alert, activating a tactile alert, cutting off power to the surgical instrument or combinations thereof.

The predefined threshold may include a first predefined threshold, and a second predefined threshold. The step of triggering an action of the navigation system may include triggering a first action when the offset distance is greater than a first predefined threshold but less than the second predefined threshold and triggering a second action when the offset distance is greater than the second predefined threshold. The action may include one of: sounding an audible alert, displaying a visual alert, activating a tactile alert, cutting off power to the surgical instrument or combinations thereof.

A surgical system is provided, including a navigation system comprising a control console and a localizer. The navigation system is in communication with first data representing a surgical instrument and second data representing a patient's anatomy. The surgical instrument includes a tool tip.

The navigation system is operable to track the surgical instrument and the anatomy in the virtual space during an operation based on information gathered by the localizer from an instrument tracker coupled to the surgical instrument and a patient tracker coupled to the anatomy. The navigation system is configured to track the surgical instrument and the anatomy and store data representing the tracked surgical instrument pose and the anatomy pose in a common coordinate system.

The navigation system is configured to determine that the tool tip is within a predefined proximity to the anatomy based on the tracked surgical instrument pose and the tracked anatomy pose. The navigation system is further configured to determine the tool tip does not depart the predefined proximity by more than a predefined magnitude over a predefined duration. The navigation system is further configured to determine an offset distance based on the tracked surgical instrument and the tracked anatomy in the common coordinate system. The navigation system is further configured to compare the offset distance to a predefined threshold.

The navigation system may include an alert device, and the navigation system may be further configured to trigger an action when the offset distance is greater than the predefined threshold. The alert device may be a footswitch, where the footswitch is operable to generate a vibration.

A method of providing navigation guidance for a surgical procedure is provided. The method includes registering a patient's anatomy in a common coordinate system. The patient's anatomy includes at least a first bone and a second bone. The method includes registering a surgical instrument in the common coordinate system. The method includes tracking the patient's anatomy and the surgical instrument with the navigation system during operation of the surgical instrument on the first bone of the patient's anatomy. The method includes determining an offset distance according to the methods disclosed herein with respect to the second bone; and tracking the patient's anatomy and the surgical instrument with the navigation system during the operation of the surgical instrument on the second bone of the patient's anatomy.

A method of performing a surgical operation is provided. The method includes coupling a patient tracker to a patient's anatomy and coupling an instrument tracker to a surgical instrument, the surgical instrument including a tool tip. The method includes operating a navigation system to register the instrument tracker and the patient tracker in a common coordinate system and to track the surgical instrument and the patient's anatomy. The method includes pausing the tool tip in contact with the patient's anatomy for a predefined duration to initiate a registration verification. The navigation system is configured to determine an offset distance based on the tracked surgical instrument and the tracked patient's anatomy. The method includes evaluating the offset distance against a predefined threshold.

The navigation system may be configured to trigger an action when the result of the evaluation of the offset distance determines the offset distance is greater than the predefined threshold, wherein the action may include one of: sounding an audible alert, displaying a visual alert, activating a tactile alert, cutting off power to the surgical instrument or combinations thereof. The method may also include providing an input to the navigation system to terminate the triggered action.

The step of pausing the tool tip in contact with the anatomy may include pausing the tool tip in contact with a first anatomy contact point at a first time. The surgical instrument may be in a first pose and have a first proximal point of the tool tip being in contact with the first anatomy contact point at the first time. The method may further include pausing the tool tip in contact with a second anatomy contact point at a second time. The surgical instrument may be in a second pose and have a second proximal point of the tool tip in contact with the first anatomy contact point at the second time. The navigation system may be configured to determine a first offset distance based on the first anatomy contact point and the first proximal point, and to determine a second offset distance based on the second anatomy contact point and the second proximal point.

The step of evaluating the offset distance may include one of: evaluating the first offset distance against the predefined threshold; evaluating the second offset distance against the predefined threshold, or combinations thereof.

The patient's anatomy may include a first bone and a second bone, and the method may further include operating the surgical instrument in application to the first bone and operating the surgical instrument in application to the second bone. The step of pausing the tool to initiate a registration verification may be performed in contact with the second bone subsequent to operating the surgical instrument in application to the first bone and prior to operating the surgical instrument in application to the second bone.

Other objects, features, and advantages of the present disclosure will be readily appreciated as the same becomes better understood after reading the subsequent description taken in connection with the accompanying drawings.

BRIEF DESCRIPTION OF THE DRAWINGS

Other advantages will be readily appreciated as the same becomes better understood by reference to the following detailed description when considered in connection with the accompanying drawings, wherein.

DETAILED DESCRIPTION

Figure 1:
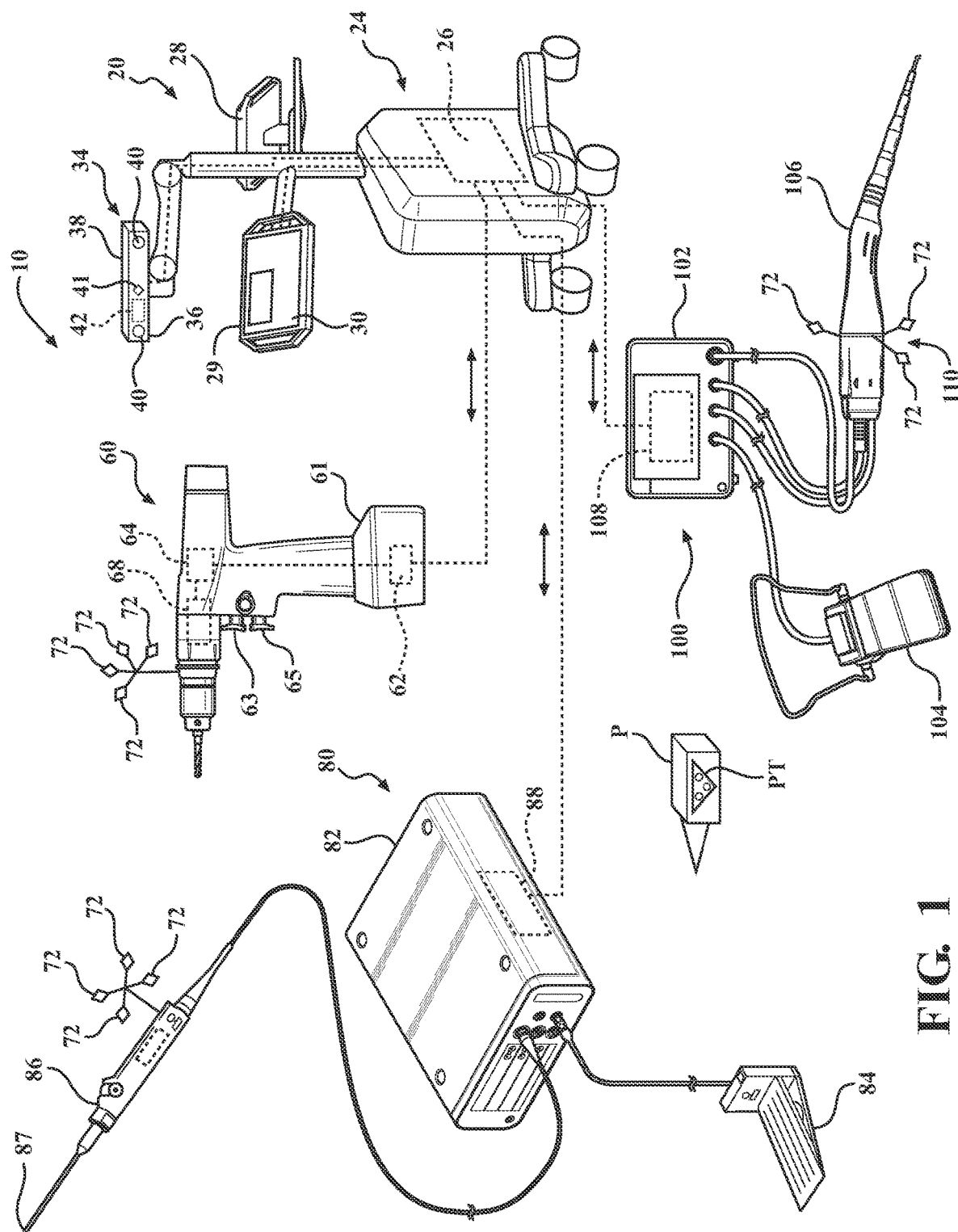
FIG. 1 is a schematic view of a surgical system comprising a suite of surgical tools for use in performing navigation-assisted surgery.

Referring to FIG. 1, a surgical system 10 comprising a suite of surgical tools for use in performing navigation-assisted surgery on a patient is illustrated. The version shown in FIG. 1 includes a surgical navigation system 20. The surgical navigation system 20 is set up to track movement of various objects in the operating room. Such objects include, for example, surgical tools and patient anatomy. The surgical navigation system 20 tracks these objects for purposes of displaying their relative positions and orientations to the surgeon, and in some cases, for alerting the surgeon of certain events or occurrences in connection with operating the surgical tools. For example, virtual cutting boundaries can be associated with the patient anatomy and the system 10 may alert the surgeon when a surgical tool approaches a cutting boundary or may deactivate a tool when a surgical tool exceeds a cutting boundary.

The navigation system 20 may include a computer cart assembly 24 that houses a navigation computer 26. A navigation interface is in operative communication with the navigation computer 26. The navigation interface includes a first display 28 adapted to be situated outside the sterile field of the surgical operation and may include a second display 29 adapted to be situated inside the sterile field. The displays 28, 29 are adjustably mounted to the computer cart assembly 24. One or more input devices (not shown), such as a keyboard, mouse, trackball, or other, can also be provided to input information into the navigation computer 26 or to otherwise select or control certain aspects of the navigation computer's 26 operation. Further, other hardware may be provided to facilitate alternative forms of input. For example, sensors may be provided at one or more of the displays to allow input through gesture control, or a microphone may be provided for voice command control.

A localizer 34 communicates with the navigation computer 26. In the illustration shown, the localizer 34 is an optical localizer and includes a camera unit 36. The camera unit 36 has an outer casing 38 that houses one or more optical sensors 40. The optical sensors 40 may be rigidly mounted to a common support structure. The outer casing may provide the common support structure for the optical sensors 40. Alternatively, a rigid support structure common to the optical sensors may be encased by, but distinct from, the outer casing 38. As illustrated in FIG. 1, the optical sensors 40 are disposed at opposite ends of the elongated camera unit 36, such that the optical sensors 40 are arranged stereoscopically relative to the surgical site.

Although described in connection with an optical localizer including camera technology for locating and tracking an object based on the sensing of electromagnetic energy in the visible or near visible spectrum, other localizing and tracking technologies may be used. For example, electromagnetic energy in the microwave or radio wave spectrums may be used instead or in addition. Likewise, sonic or ultrasonic energy may be another alternative technology for locating and tracking an object. The common feature of these technologies useful for tracking and locating an object is that energy can be generated or reflected at the objects to be tracked and sensed by the navigation system for determination on the object's location.

In some alternatives, such as the one shown in FIG. 1, two optical sensors 40 are employed. In other alternatives, additional optical sensors may be provided, further separated from the first set of optical sensors 40 to ensure unobstructed views of the surgical sites and the trackers present therein. The optical sensors 40 are capable of variable attenuation of radiant energy, for example, light, into signals as small bursts of electrical current that can be conveyed as information between electronic devices.

The camera unit 36 may also, or alternatively, include a video camera 41 or other additional sensing devices (not shown). The video camera 41 may include similar or different optical sensing technology as that employed in the optical sensors 40. For example, the optical sensors 40 may be adapted to sense energy in the infrared or near-infrared spectrum, while the video camera 41 may be adapted to send light in the visible spectrum.

The optical sensors 40 may be separate charge-coupled devices (CCD). In some alternatives, two, two-dimensional CCDs are employed. In some cases, the optical sensors 40 are arranged for stereoscopic operation. In other alternatives, the optical sensors 40 may be single cameras combined with depth sensors, laser range finders, and the like. It should be appreciated that in other alternatives, multiple, separate camera units 36, each with a separate CCD, or two or more CCDs, could also be arranged around the operating room. Additional optical sensors assist in ensuring that the navigation system 20 maintains an unobstructed view of the surgical site through one or more of the optical sensors 40 throughout the surgical operation. The optical sensors 40 may include CCDs capable of detecting infrared (IR) radiant energy. The optical sensors may employ other sensing technology, including, but not limited to, complimentary metal-oxide semiconductor (CMOS) active-pixel sensors, and the like.

The camera unit 36 may be mounted on an adjustable arm or other articulated support structure of the cart assembly 24 to selectively position the localizer 34 with a field of view, preferably unobstructed, of the target space including the surgical site within which the patient anatomy and trackers (as discussed below) will be positioned. In some cases, the camera unit 36 is adjustable in at least one degree of freedom by rotating about a rotational joint. In other alternatives, the camera unit 36 is adjustable about two or more degrees of freedom. Where multiple camera units 36 are employed, each may be individually mounted for selective positioning about the surgical setting. Alternatively, the cart structure 24 may support multiple adjustable arms to support multiple camera units 36.

The camera unit 36 further includes a camera controller 42 in communication with the optical sensors 40 to receive signals from the optical sensors 40. The camera controller 42 communicates with the navigation computer 26 through either a wired or wireless connection (not shown). One such connection may be an IEEE 1394 interface, which is a serial bus interface standard for high-speed communications and isochronous real-time data transfer. Other suitable connection types may include Ethernet, thunderbolt, USB interface, PCI express, DisplayPort, or the like. The connection could also use a company-specific or proprietary protocol. In other alternatives, the optical sensors may communicate directly with the navigation computer 26, such that the navigation computer incorporates the functionality of, and thus operates as, the camera controller 42. Processing of the signals from the optical sensors may occur at the camera controller 42. Alternatively, the camera controller 42 may communicate the signals to the navigation computer 26 for processing. In communicating the signals to the navigation computer 26 for processing, the camera controller 42 may perform some pre-processing conditioning, reformatting, translating, or the like.

The navigation computer 26 may be a personal computer or laptop computer. The navigation computer 26 communicates with the displays 28, 29, and has a central processing unit (CPU), and other processors, memory units, data storage units and combinations thereof. The navigation computer is provided with software as described below. The software converts the signals received from the camera unit 36, from the camera controller 42 or the optical sensors 40, into data representative of the position and orientation of the objects being tracked. Position and orientation signals, or data derived from those signals, are used by the navigation computer 26 for the purpose of tracking objects. The cart assembly 24, display 28, and camera unit 36 may be like those described in U.S. Pat. No. 7,725,162 to Malackowski, et al., issued on May 25, 2010, entitled "Surgery System," hereby incorporated by reference.

The surgical system 10 including the navigation system 20 may be adapted for operation with a variety of surgical tool systems. FIG. 1 illustrates representative available tool systems, but it should be understood that other options are available or may become available in the future without deviation from the scope of the present disclosure.

The surgical system 10 may be used in connection with a cordless power tool. The cordless power tool may include a sagittal saw, reciprocating saw, rotary drill, sternum saw, or the like. In the illustration in FIG. 1, the cordless power tool is shown as a cordless power driver 60. It should be understood corded power tools may also be used. One example of such a cordless power driver 60 tool is the System 8 Cordless Driver sold by Stryker. The driver 60 includes a battery unit 61 which provides power to the driver 60. The battery unit 61 can include a rechargeable battery pack. The battery unit 61 may be a smart battery pack, including a data module 62 which has electronics and programming to facilitate communication between the driver 60 and the navigation computer 26.

The driver 60 may include a driver controller 64 in operative communication with the data module 62. Alternatively, a single computer module may be provided that provides the functionality of both the driver controller 64 and the data module 62. The driver controller 64 controllers the operation of the driver 60, being in communication with input controls, such as triggers 63, 65, the driver motor 68, and other sensors or instrumentation included within the driver 60. In one example, a temperature sensor is included so that an overheating driver motor 68 can be detected and operation of the driver 60 disabled by the driver controller 64.

The driver 60 is provided with a tracker 70. The tracker 70 may be an active tracker or a passive tracker. Active trackers require a power source and have an array of markers 72 (also referred to as tracking elements or fiducials) that actively generate and emit radiation in a wavelength detectable by the optical sensors 40. The markers 72 of an active tracker may be a light emitting diode (LED), including for example, an infrared LED. The array of active markers may be "always on" or may be operatively "on" to selectively fire (that is, emit radiation) in response to commands from the surgical navigation system 20. In such selective-fire active trackers, the tracker may communicate by way of a wired or wireless connection with the navigation computer 26 of the surgical navigation system 20. The active tracker may be powered with an internal battery or may have leads to receive power from an externally-connected source.

Alternatively, the tracker 70 may be a passive tracker. That is, the array of markers 72 may reflect ambient radiant energy or radiant energy that has been emitted into the target space. For example, the camera unit 36 may be equipped with one or more infrared LEDs to emit infrared energy to be reflected by the markers 72 and thereafter sensed by the optical sensors 40. The passive tracker typically does not require a power source.

Although described with reference to optical technologies, including light reflective or emitting markers, other trackers may be used consistent with the sensing technology of the localizer. For example, the localizer may include an electromagnetic field generator, and the trackers may employ coils or coil arrays. An example of the use this technology can be appreciated from the disclosure of U.S. Pat. No. 8,249,689 B2, entitled "Coil Arrangement for Electromagnetic Tracking Method and System," the entirety of which is incorporated by reference.

The surgical system 10 may also be used with a universal integrated console or an instrument platform. The universal platform 80 comprises a console 82, a footswitch 4, and a powered surgical instrument 86. The console 82 controls and provides power to a connected instrument 86. The instrument 86 may be a small bone orthopedic saw or drill, a high speed drill (for example for neuro applications, or for spinal applications), an ENT shaver, joint shaver, bone mill or the like. One example of such a universal platform is the Core 2 Console powered instrument driver, and related tools, sold by Stryker and described in the International Application Publication PCT WO 2015/021216 A1, entitled "System And Method For Driving An Ultrasonic Handpiece As A Function Of The Mechanical Impedance Of The Handpiece," the entirety of which is incorporated by reference. The console 82 includes a data module 88 which facilitates communication between the console and the navigation computer 26.

Similar to the driver 60 described above, the instrument 86 is provided with a tracker 90. The instrument tracker 90 is similar to the driver tracker 70 and includes an arrangement of markers 72. The markers 72 may be active or passive, and are sensed by the camera unit 36 to track and monitor the position and orientation of the instrument 86.

The surgical system 10 may also be used with an ultrasonic aspirator system 100. The ultrasonic aspirator system 100 comprises a console 102, a footswitch 104 and aspirator tool 106. The console 102 controls and provides power to a connected aspirator tool 106. One example of such an ultrasonic aspirator system is the SONOPET iO Ultrasonic Aspirator sold by Stryker. The console 102 includes a data module 108 which facilitates communication between the console and the navigation computer 26.

The tool 106 is provided with a tracker 110, similar to the instrument tracker 90 and the driver tracker 70. The tool tracker 110 includes an arrangement of markers 72, which may be active or passive, as discussed above, to be sensed by the camera unit 36 for tracking and monitoring the tool's 106 position and orientation. As can be seen in FIG. 1, the driver tracker 70, instrument tracker 90, and tool tracker 110 are distinguishable based on their arrangement of markers 72. Descriptions provided herein, and designations such as "tool tracker" or "instrument tracker" are not intended to be limiting but are simply used to differentiate among the surgical articles available for use with the present disclosure.

The trackers may be attached in the manner shown in U.S. Pat. No. 7,725,162 to Malackowski, et al., issued on May 25, 2010, entitled "Surgery System," the disclosure of which is hereby incorporated by reference. Alternatively, the Trackers could be attached like those shown in U.S. Pat. No. 9,566,120 to Malackowski, et al., issued Feb. 14, 2017, entitled "Navigation Systems and Method for Indicating and Reducing Line-of-Sight Errors," the disclosure of which is hereby incorporated by reference. In yet further alternatives, the trackers may be attached in other ways as is conventional in the art.

Although shown as distinct structures mounted on and extending from the surgical articles, the trackers may alternatively be integrated into the structure of the article itself. For example, the markers 72 may be formed directly into the structure of the tool or instrument to be tracked. In yet further alternatives, structures or features of the article itself may be used as a tracker, omitting dedicated markers. In such cases, surfaces or edges of the article may be recognizable to the navigation system and used to track the position and orientation of the article. Still further, markings or patterns may be included on a surface of the article and used as a tracker. For example, a linear barcode, or 2D barcode (also known as a QR code) can be featured on a surface of the article that will remain visible to the camera unit 36 throughout the surgery for tracking the article.

Figure 2:
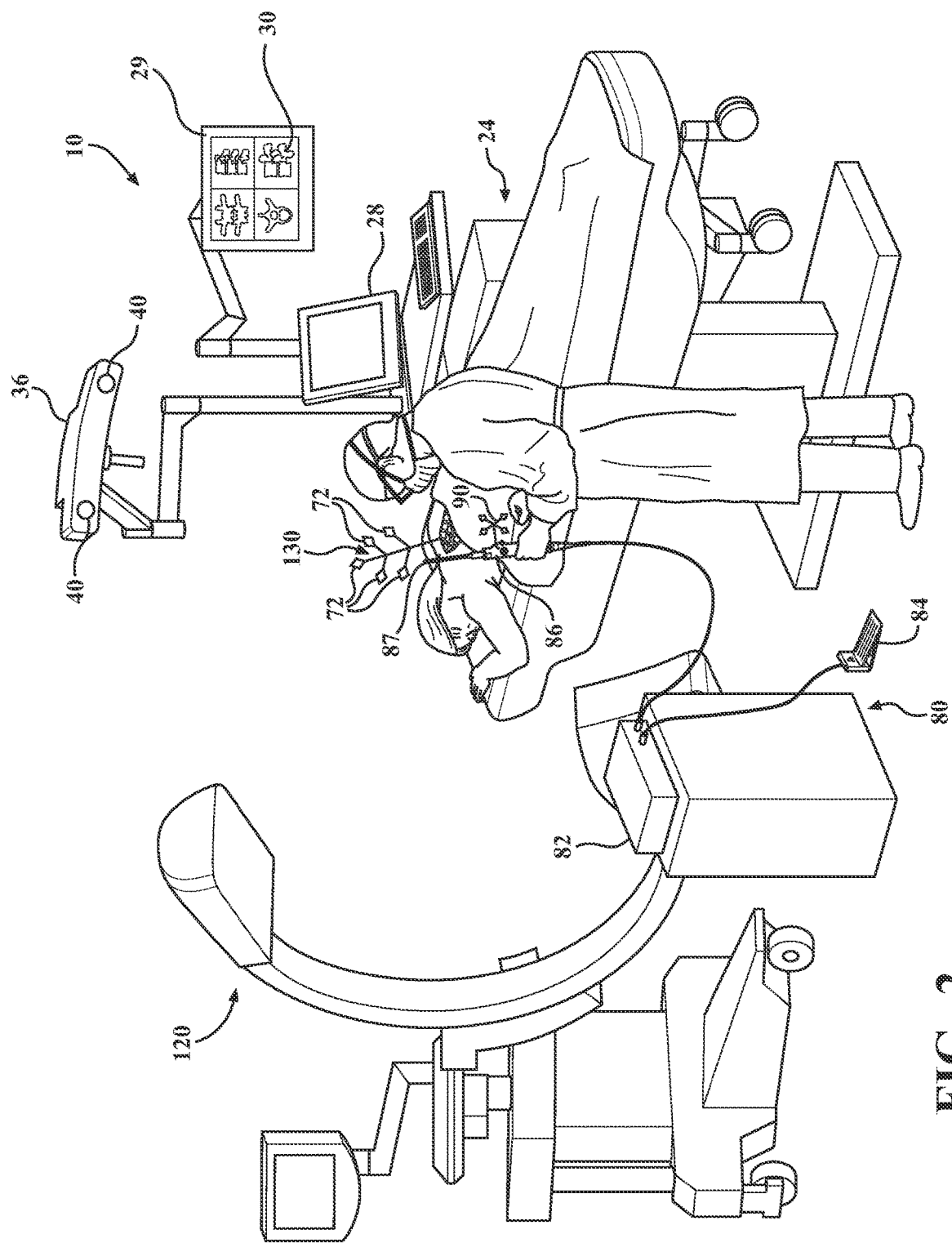
FIG. 2 is a perspective view of a navigation system being used with a surgical tool in performing navigation-assisted surgery.

Turning now to FIG. 2, the surgical system 10 is illustrated in an exemplary surgical environment for use with a universal tool platform 80, including console 82, footswitch 84 and instrument 86. Also provided at the surgical site is a C-arm computerized tomography (CT) system 120 for providing intraoperative imaging of the patient's anatomy. Although illustrated with a CT system 120, other imaging technology may be employed for intraoperative imaging, including MRI, X-Ray, or videography. Generally, regardless of the technology chosen, the imager is in communication with the navigation computer 26. Information from the imager is used to prepare a virtual representation of the patient's anatomy, such as a 3D model of the tissue to be treated in the surgery. The process of preparing the virtual representation can be through segmentation of the image data. The segmentation can be an automated process, for example, through machine learning. Example processes are disclosed in U.S. Pat. No. 10,198,662 B2, issued Feb. 5, 2019, and entitled Image Analysis; and U.S. Pat. No. 8,867,809 B2, issued Oct. 21, 2014, and entitled Image Processing Method. Using the information from the imager and affixing a further tracker onto the tissue to be treated, the patient tracker 130, a model of the tissue can be represented in the navigation system 20 and tracked during the course of the surgical operation.

Initially, the objects to be located and tracked during the surgery are viewed by the optical sensors and identified. The objects may be identified by selecting the objects to be tracked and using an input device connected to the navigation computer 26. The navigation computer 26 may store detailed information regarding numerous objects in memory or data storage on the navigation computer 26 and the user may be able to manually select the objects to be tracked from a database of objects.

Additionally, or alternatively, the navigation computer 26 may identify the objects to be tracked based on a pre-operative surgical plan. In this case the navigation computer 26 may have a preset list of workflow objects that may be used in a pre-scripted surgical workflow. The navigation computer 26 may actively search for and locate the workflow objects using software. For instance, groups of pixels associated with different sizes and shapes of the various objects may be stored in the navigation computer 26. By selecting or identifying the objects to be located and tracked, the software identifies the corresponding group of pixels and the software then operates to detect like groups of pixels using conventional pattern recognition technology.

Additionally, or alternatively, the objects to be located and tracked can be identified using an interface in which one of the users outlines or selects the objects to be tracked on one or more displays 28, 29. For instance, images taken by the optical sensors 40, or a video camera, 41 of the surgical site may be displayed on one or more of the displays 28, 29. The user then, using a mouse, digital pen, or the like, traces objects to be located or tracked on the display 28 or 29. The software stores the pixels associated with the object that was traced into its memory. The user may identify each object by a unique identifier, such as naming the object using the software, so that the saved group of pixels may be associated with the unique identifier. Multiple objects could be stored in this manner. The navigation computer 26 utilizes conventional pattern recognition and associated software to later detect these objects. The navigation system 20 is able to detect movement of these objects by continually taking images, reviewing the images, and detecting movement of the groups of pixels associated with the objects.

In conventional surgical navigation systems, the objects to be tracked are initially registered using a navigation pointer P. For example, the navigation pointer P may have an integrated tracker PT. The navigational computer 26 may store initial data corresponding to the location of the tip of the pointer P relative to the pointer tracker PT such that the navigation system 20 is able to locate and track the tip of the pointer P in the localizer coordinate system LCLZ. Accordingly, prior to the start of the surgical procedure once all the objects are located in their desired locations, one of the users may touch all of the objects with the pointer P, while identifying the objects in the navigation system 20 using one of the input devices described above. So, for example, when the user touches the instrument 86 with the tip of the pointer P the user may simultaneously trigger collection of that point in the localizer coordinate system LCLZ (via another input device, such as a foot pedal). When the point is collected the user can also enter into the navigation software the identity of the object (via typing, pull-down selection from a list of objects, etc.).

As illustrated in the Figures, the camera unit 36 receives optical signals from the markers 72 of the trackers 70, 90, 110, and outputs to the navigation computer 26 signals relating to the position of the trackers relative to the localizer 34. Based on the received signals, the navigation computer 26 generates data indicating the relative positions and orientations of the trackers 70, 90, 110 relative to the localizer 34.

Prior to the start of the surgical procedure, additional data are loaded into the navigation computer 26. Based on the position and orientation of the trackers 70, 90, 110, and the previously loaded data, such as virtual object data representing the geometry of the object to which the tracker is attached, the navigation computer 26 determines the position of the working end of the surgical article (e.g., drill point, aspirator tip, etc.) and the orientation of the article relative to the tissue against which the working end is to be applied.

The navigation computer also generates information that indicates the relative position of the surgical instrument's working end to the tissue. This information can be rendered into useful imagery and applied to the displays 28, 29. Based on the display, the user is able to view the relative position of the surgical instrument working end to the tissue in the surgical site. The displays 28, 29, as discussed above, may include a touch screen 30 or other input/output device that allows the entry of commands.

Figure 3:
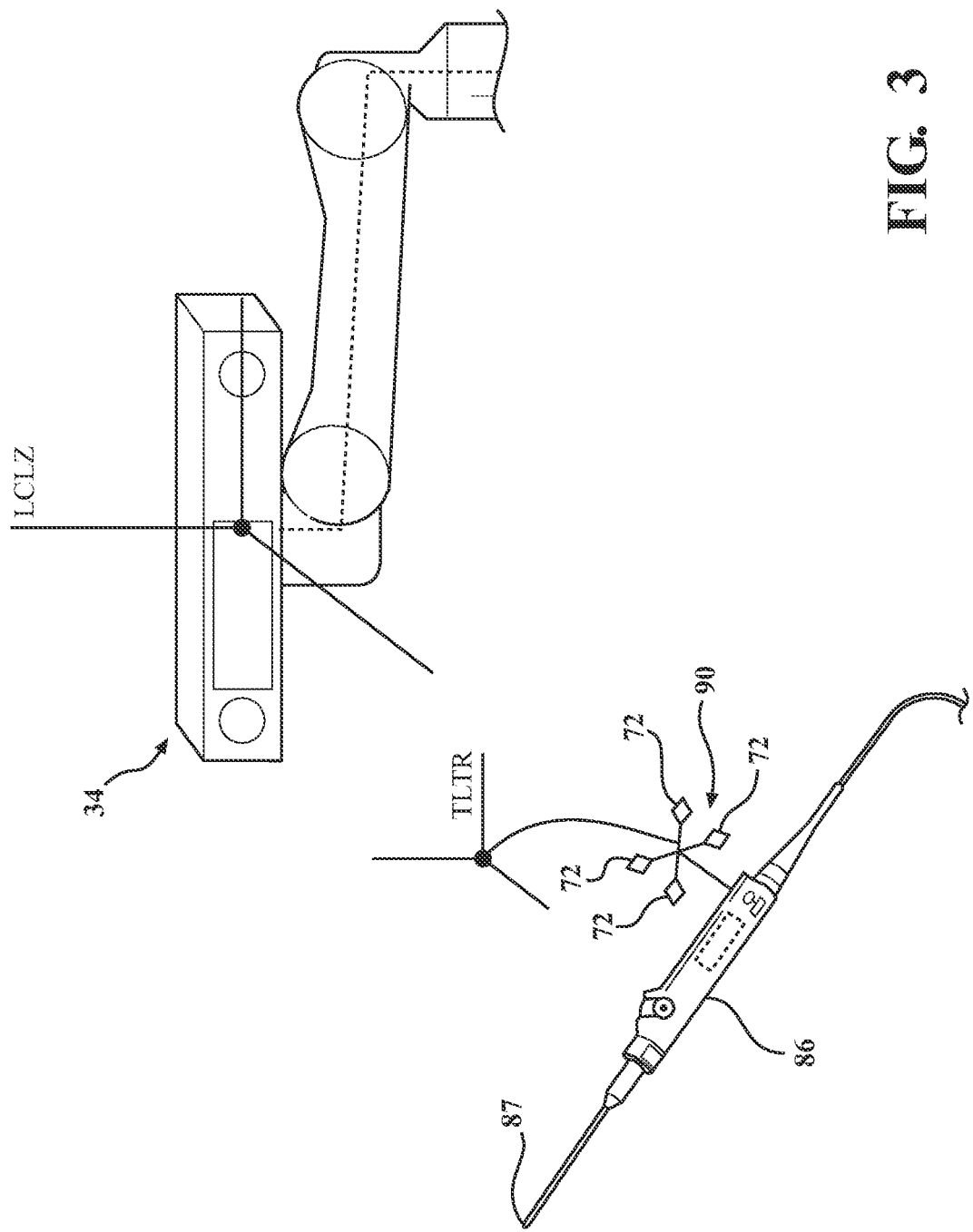
FIG. 3 shows the localizer coordinate system and a tracker coordinate system of a tracker coupled to a surgical instrument.

Referring now to FIG. 3, tracking of objects in the surgical site is generally conducted with reference to a localizer coordinate system LCLZ. The localizer coordinate system has an origin point and an orientation defining relative x-, y-, and z-axes. During the surgical operation, it is preferable to keep the localizer in a stationary position. An accelerometer (not shown) mounted to the camera unit may be used to track sudden or unexpected movement of the localizer coordinate system LCLZ, as may occur when the camera unit 36 is inadvertently bumped by surgical personnel.

Each tracker 70, 90, 110, associated with a surgical article or a patient's anatomy has its own coordinate system separate from the localizer coordinate system LCLZ. As depicted in FIG. 3, the coordinate system associated with the tool tracker 90 has its own origin point and orientation defining relative x-, y-, and z-axes. The navigation system 20, through the localizer 34, monitors the position and orientation of the surgical articles and the patient's anatomy by computing the relative change of the trackers' origin point and orientation relative to the localizer coordinate system.

During the initial phase of the surgical procedure, the trackers are affixed to the articles (if not provided in manufacturing) and the anatomy to be tracked. The pose of each such item must be mapped to the coordinate system of the tracker to that item. This registration or calibration step creates a fixed relationship between the virtual representation of the geometry of the tracked article to the coordinate system of the associated tracker. In this way, sensed movement of a tracker can be represented virtually with a corresponding movement of the tracked article by the navigation computer 26 relative to the other tracked articles in the common coordinate system, for example, of localizer LCLZ.

While navigation systems have been used with robotically controlled surgical systems, improved method are needed to provide navigation guidance for manually performed surgeries using powered surgical tools. In accordance with the present disclosure an improved method of navigating a surgical instrument is provided to verify the position of the instrument tool tip relative to the patient anatomy.

In a first example case, the surgical instrument includes a variable speed motor, such as driver motor 68. The variable speed motor is controlled by a controller. For example, the variable speed motor may receive a control signal from the driver controller 64 in the case of the power driver 60. In another example, in the case of the universal tool platform 80, the control signal controlling the variable speed motor in the instrument 86 may come from the universal console 82. The following descriptions may be put in the context of a particular tool or tool type. This is not intended to be limiting and the methods and systems may be practiced with other presently-known or future developed surgical tools, tool systems or the like. Moreover, the steps of one method may be practiced in the context of any other method and the features of one disclosed system may be practiced with any other without departing from the scope of the present disclosure.

Although described in the previous paragraph with respect to a control signal for a variable speed motor, this is not limiting, and other alternative actuators are contemplated within the scope of the present disclosure. For example, in the case of the ultrasonic aspirator, a variable speed motor is not employed, but rather a control signal from the aspirator console 102 may control the operation of the aspirator tool 106. The aspirator tool 106 includes a hollow tip which oscillates longitudinally along its axis, driven, for example, by a piezoelectric transducer as the actuator of the tool. The oscillation occurs at a frequency corresponding to ultrasound. The longitudinal vibration of the tip destroys cell membranes by its hammering effect. Since the high-frequency vibration generates heat, a protective sheath carries fluid to irrigate the tip. Irrigation intensity can be changed as needed to modulate the application of heat from the tip to the tissue. When irrigation is low, heat developed by ultrasonic aspiration can be used for cutting or coagulating purposes. Suction can also be provided through the aspirator tool 106 to remove fragmented tissue as well the irrigation through the tip. By monitoring the operating characteristics of the control signal, the system can detect when the tool tip is operating in free space or is operating in contact with the tissue.

Regardless of surgical article type, operating the article while it is in free space may be characterized differently from operating the article while it is in contact with a patient's anatomy, including bone or soft tissue such as skin. In the case of a powered driver 60, or other article having a variable speed motor, a power supplied to the motor will result in a certain rotational speed when operating in free space. When there is resistance applied against the rotation of the motor, such as when a drill, bur, or other tool type, is in contact with tissue for material removal, the rotational speed may be decreased unless the power supplied to the motor is adjusted. For example, the current or voltage may be increased during cutting in order to maintain a constant rotational speed relative to when the tool is not in contact with any tissue. Likewise, tools employing other actuators, and not driven by a motor, may operate under a first condition when not in contact with tissue and may operate under a second condition, different from the first when in contact with tissue. Such non-motor driven tools are likewise contemplated to be practiced with the described methods and systems disclosed herein.

The controller driving the surgical article provides the control signal to operate the article and also is in communication with sensors on the article to monitor the operating condition. For example, in the power driver 60, the driver controller 64 may receive signals indicating the driver motor's 68 instantaneous rotational speed, applied power, voltage, current, temperature, or otherwise. This signal may be received by the controller at a frequency of several times per second. For example, the frequency may be about 60 Hz, about 100 Hz, about 1000 Hz, or other suitable frequency. In other examples, not employing a motor, such as the ultrasonic aspirator system 100, the controller—in this case the aspirator console 102—may receive one or more signals indicating the operating condition of the article, i.e., the aspirator tool 106. Specifically, the aspirator console 102 may monitor the temperature at the tool tip, the flow rate of the irrigation through the tool tip, the vacuum applied to the suction, or otherwise.

The controller may be equipped with memory or data storage or may be in communication with memory or data storage, so that the operating condition may be recorded relative to the time of the recording. The controller may begin recording the operating condition when the surgical article begins operating and may continue throughout the duration of the operation. The controller may analyze the monitored operating condition to define a first characteristic operating condition for when the surgical article is operating not in contact with the patient's anatomy; and may further define a second characteristic operating condition for when the surgical article is operating while in contact with the patient anatomy. The monitored operating condition may be defined according to the specific tool. For a motor driven tool, the operating condition may be an applied power, a current, a voltage, a rotational speed, or otherwise.

As described above, the navigation system 20 tracks and monitors the position of the surgical article and the patient's anatomy throughout the surgical operation. The navigation system 20, through navigation computer 26, is in communication with the one or more controllers controlling the surgical articles employed in the surgical operation. Utilizing the monitored operating condition of the surgical article, the tracked position of the surgical article can be verified, and an error condition determined, if necessary.

The navigation system 20 maintains a virtual representation of the surgical articles and the patient's anatomy to illustrate and visually render their relative positions on the displays 28, 29. However, during the surgery, trackers may become displaced. Tool wear or tissue removal from the patient may alter the fidelity of the virtual models to their physical counterparts. Therefore, the accuracy and the reliability of the virtual representation in the navigation system 20 to the surgical operation may be adversely affected. Comparing the virtual representations in the navigation system 20 to the operating condition can provide an important verification of the systems accuracy. Specifically, if the navigation system 20 shows that the virtual model of the surgical article is in contact with the patient's anatomy, but the operating condition indicates that there is no contact between the article and the anatomy, an error condition may be determined, and appropriate corrective action taken.

Figure 4A:
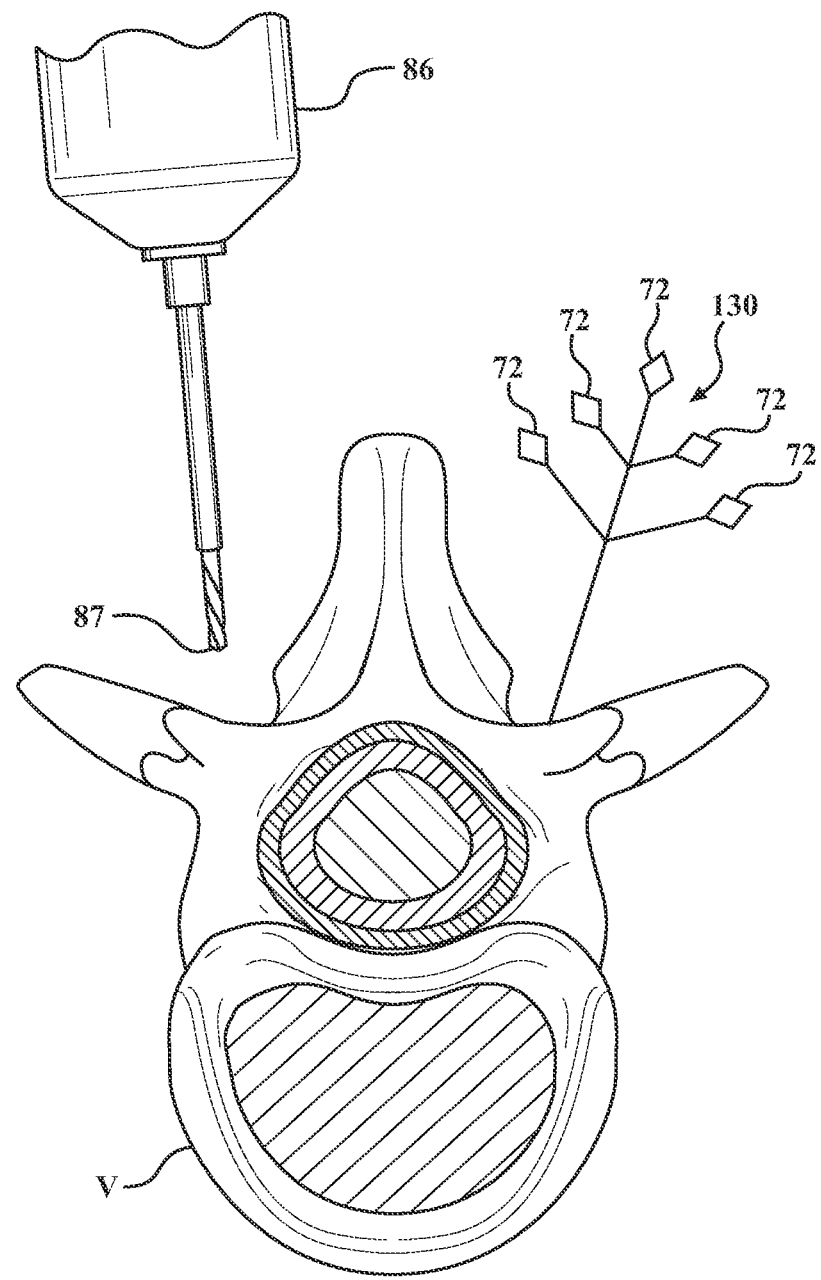
FIG. 4A shows a surgical instrument and a bone in a first relationship.

FIG. 4A shows a surgical article and a patient's anatomy in a first relationship where there is no contact between the surgical article and the anatomy. In the example shown, the surgical article is the instrument 86, and specifically, that portion of the instrument 86 including the tool tip 87. The patient's anatomy shown in FIG. 4A that will be the target of the surgical operation is a bone, vertebra V. The instrument 86 may be energized by the universal console 82, which likewise monitors parameters of the operation of the instrument 86, including the power, voltage, current, and/or rotational speed of the instrument 86. As shown in FIG. 4, the instrument 86 will have a first operation that can be characterized by the console 82 according to the monitored parameters for operation in free space—that is, not in contact with the bone, vertebra V.

Figure 6:
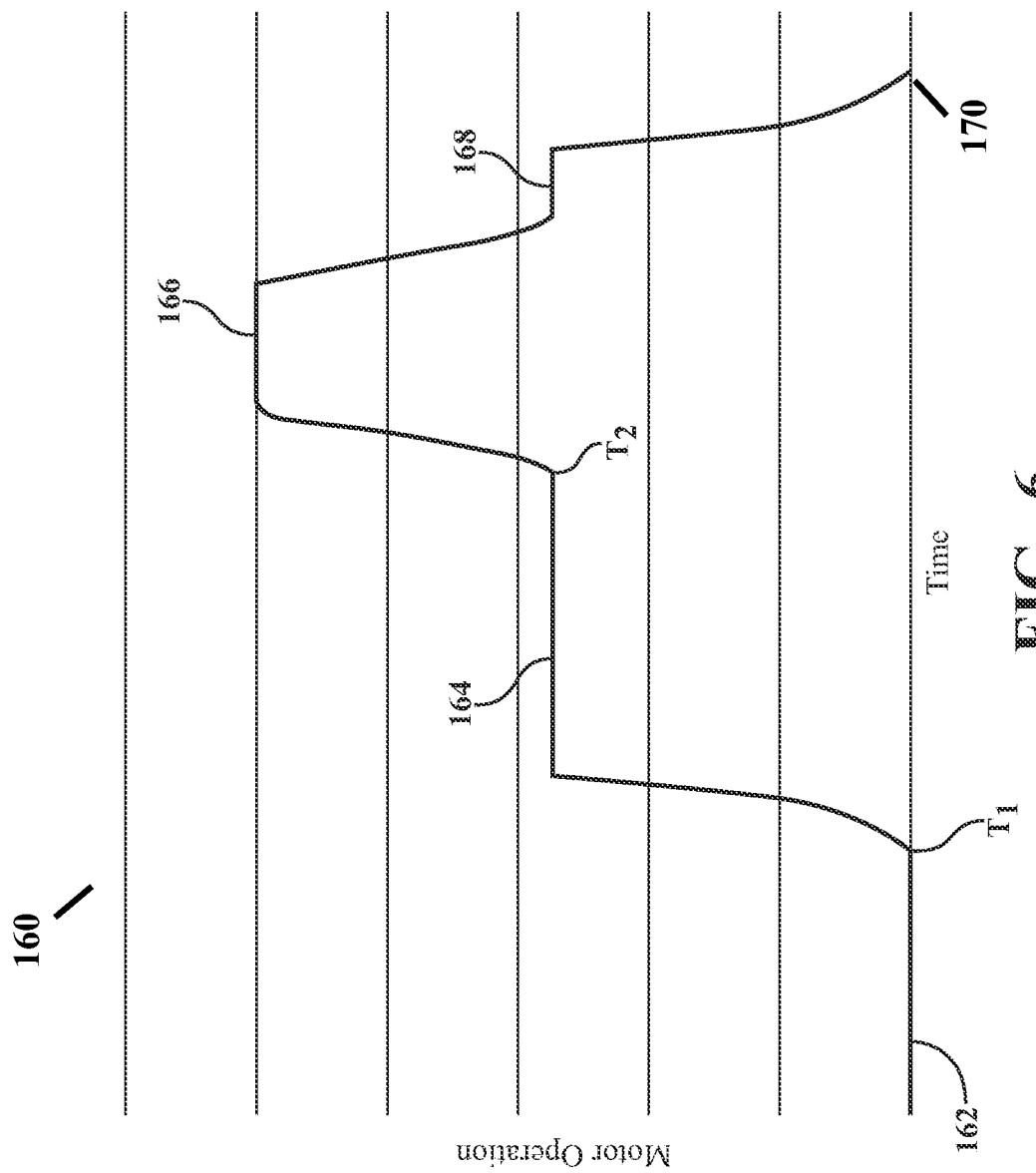
FIG. 6 shows a chart of actuator operation over time for a cutting operation.

An exemplary graph 160 of a motor operation over time is shown in FIG. 6. In a first phase 162, the instrument is unpowered, so the motor operation is static at the lowest level. At some time later $T_1$, the instrument is powered on and spins up to a first operation state 164, before being brought into contact with the patient's anatomy at $T_2$. While in contact with the patient's anatomy during the surgical procedure, the motor operation is at the higher level 166. The instrument may be removed from contact with the anatomy after the procedure 168 and then returned to an unpowered state 170.

Figure 4B:
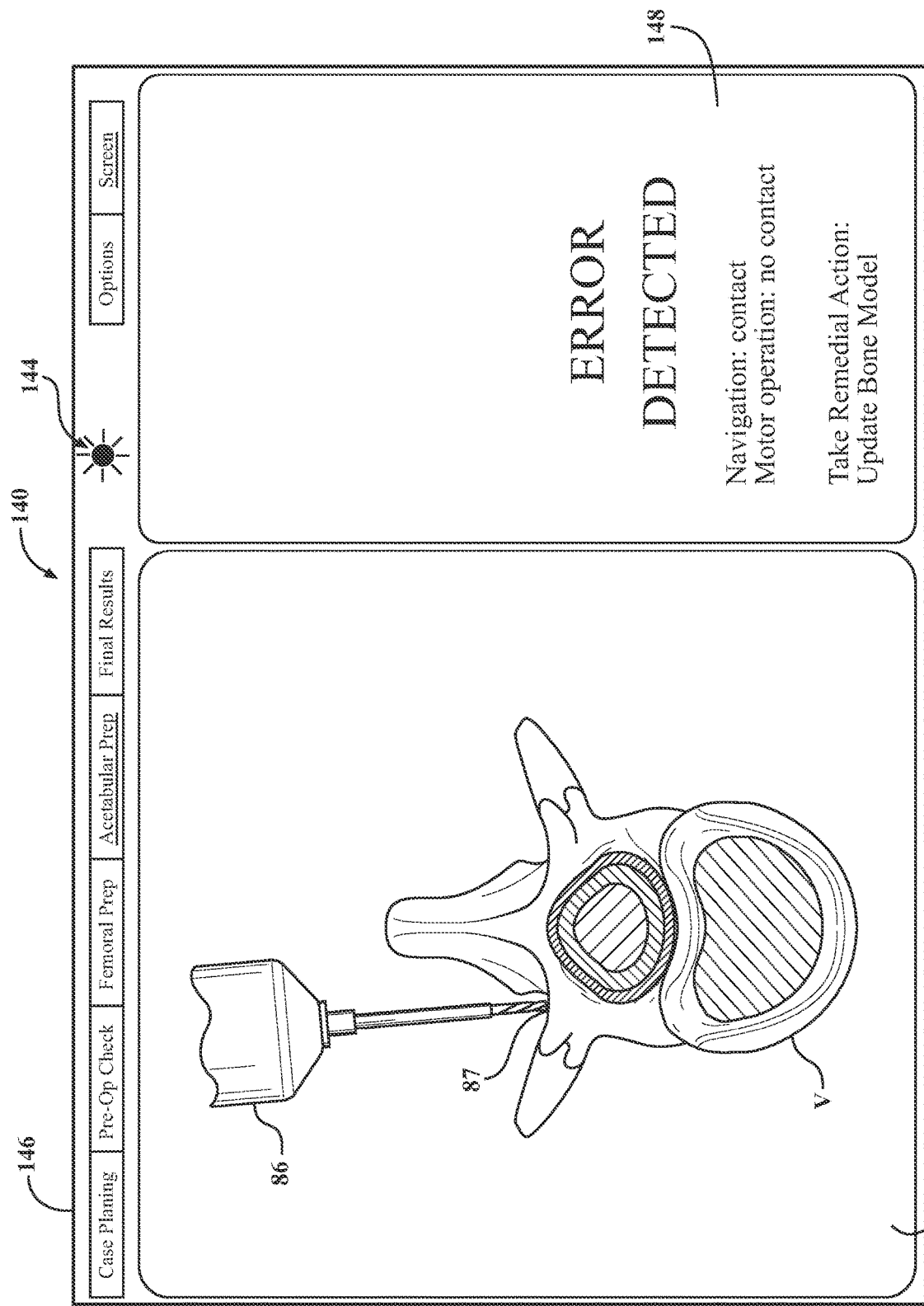
FIG. 4B shows a representation of the navigation display for the relationship shown in FIG. 4A in a first error condition.

An example user interface 140 displayed by the navigation system 20 is illustrated in FIG. 4B. The navigation system 20 computes the relationship between the instrument 86 and the bone, vertebra V, to be in contact. The user interface 140 may be divided into separate sections on the display with different information displayed in the separate sections. In a first section 142 of the user interface 140, a virtual representation of the surgical article and the patient's anatomy is shown based on (1) the models of those items, which may be stored in the memory of the navigation system 26, and (2) the relevant locations of the surgical article and the patent's anatomy that are computed based on the data sensed by the optical sensors 40 reading the instrument tracker 90 and patient tracker 130.

The navigation system 20 can compare the computed relationship of the surgical article to the patient's anatomy as being in contact or not in contact against the monitored operation parameters to verify the accuracy of the navigation guidance. In the example illustrated in FIGS. 4A and 4B, an error condition is present where the navigation system 20 calculates the tool tip 87 of the instrument 86 to be in contact with the vertebra V, but the monitored operation parameters correspond to the instrument 86 being in a relationship as shown in FIG. 4A where there is no contact between the tool tip 87 and the vertebra V.

The navigation system 20 or the console 82 can trigger an action in response to the determination of an error condition. A visual alert 144 may be activated, for example, in a toolbar region 146 of the user interface 140. The visual alert 144 may be a flashing, or blinking indicator light on the displays 28, 29. Other visual alerts may include, in the alternative or in combination, indicator lights on the console 82, on the computer cart assembly 24, on the camera unit 36, or elsewhere. Other visual alerts may take the form of prompts for user action, information displays, or other shapes, forms, pictures or otherwise.

Other actions can also be triggered in response to the determination of an error condition. A triggered action may include displaying specific information about the error condition, suggesting remedial action to correct the error condition, or combinations thereof. In FIG. 4B, error information 148 may be displayed in a region of the user interface 140 separate from the first section 142. The error information 148 may indicate that an error has been detected. The error information 148 may indicate the nature of the error— in this case that the navigation system 20 has calculated that the instrument 86 is in contact with the bone, vertebra V, but that the motor operation indicates that there is no contact between the tool and the bone. The error information 148 may indicate, in the alternative or in combination, that remedial action is advised, and further, what a preferred remedial action may include for a particular condition. In the case where the navigation system calculates contact between the bone and the tool, but the motor operation indicates no contact, the remedial action may require updating the bone model to reflect that tissue has been removed from the bone and that the actual bone surfaces are no longer reflected by the virtual model.

The triggered action upon detection of an error condition may, in addition or in the alternative to the visual alert, include other actions. The triggered action may include one or more of sounding an audible alert, activating a tactile alert, cutting off power to the surgical instrument, or combinations thereof. Sounding an audible alert can include any kind of sound alarm, beep, buzzer or the like. Displaying a visual alert may include displaying a prompt on one or more of the displays 28, 29 of the navigation system 20 that indicates the nature of the error condition determined. Activating a tactile alert may include energizing a vibratory feature of the instrument or the footswitch, or both. The vibration may be characterized as a pattern of vibrations associated with the type of error so that the user can distinguish among different types of errors based on the type of vibration alone.

Figure 5A:
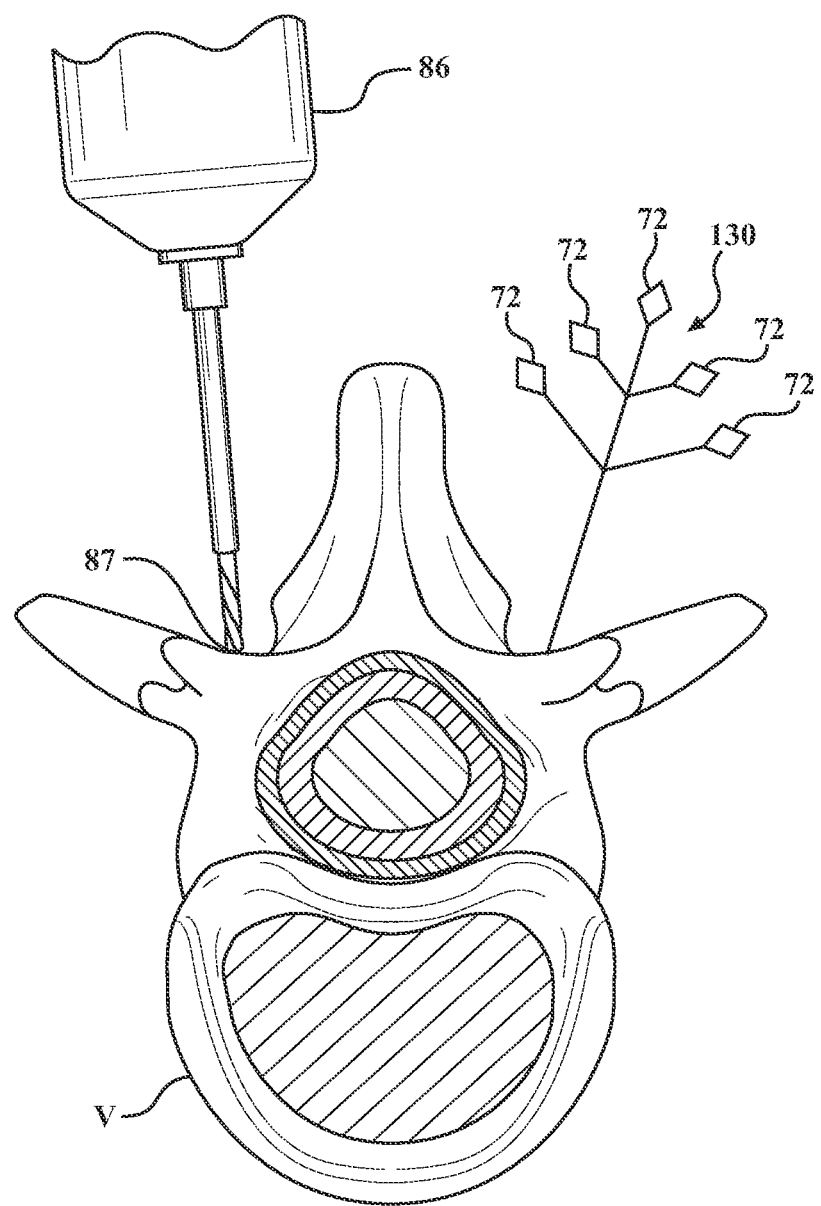
FIG. 5A shows a surgical instrument and a bone in a second relationship.
Figure 5B:
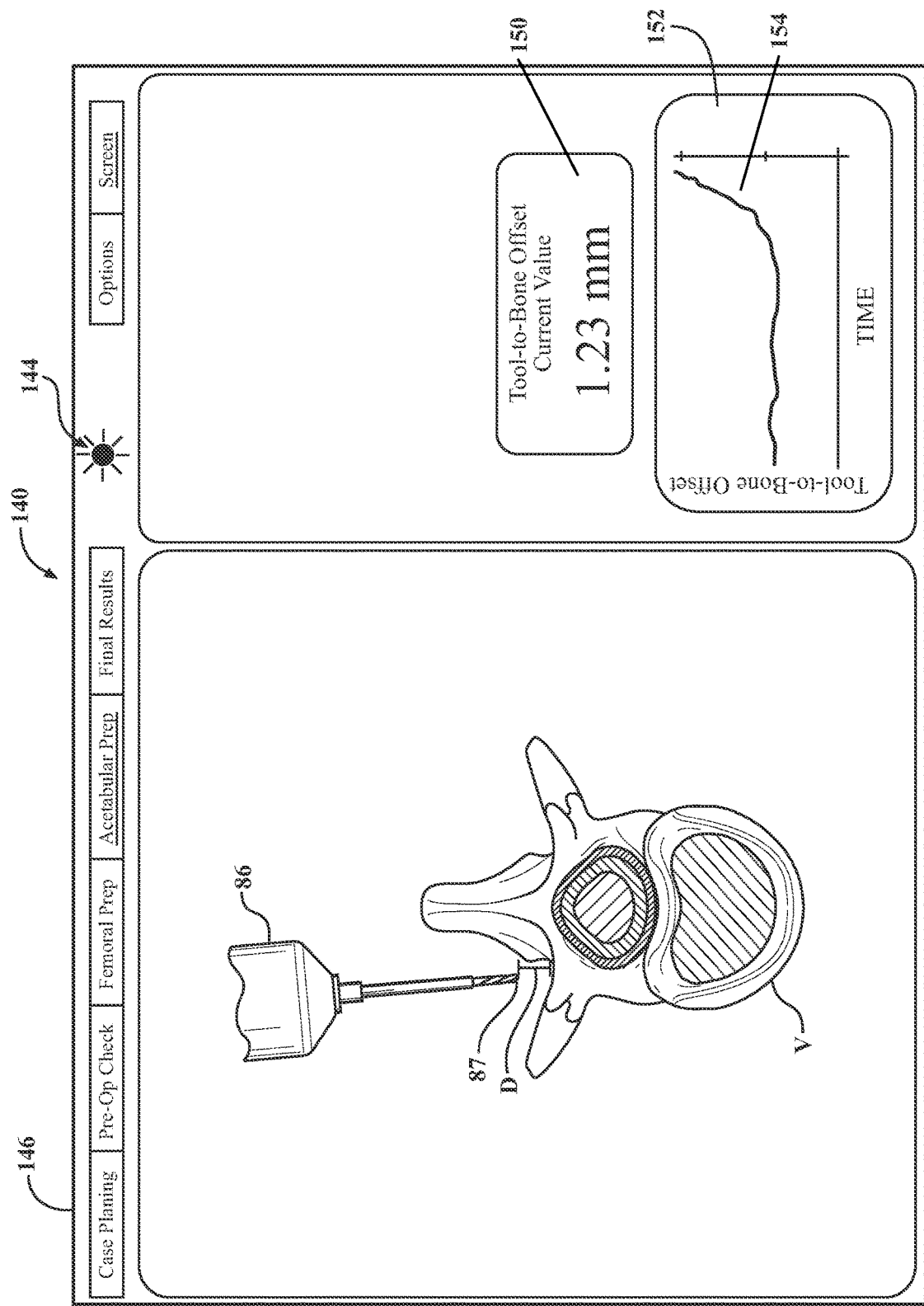
FIG. 5B shows a representation of the navigation display for the relationship shown in FIG. 5A in a second error condition.

FIGS. 5A and 5B illustrate another situation. In FIG. 5A, the tool tip 87 of instrument 86 is in contact with the bone, vertebra V. In this situation, the motor operation is at the higher level 166 of monitored motor operation shown in FIG. 6. At time $T_2$, the console 82 registers that the motor operation has deviated from the first operation state 164 corresponding to operation in free space, that is, where the instrument 86 tool tip 87 is not in contact with the bone. The console may communicate with the navigation computer 26 to evaluate the computed locations for the tool tip and the bone, based on the optical sensor data corresponding to the tool tracker 90 and the patient tracker 130 to determine a tool-to-bone offset D. At the time $T_2$, the navigation system measures the distance D between the calculated position of the tool tip 87 and the nearest surface of the bone, vertebra V, in the direction longitudinally along the length of the instrument 86. This distance is the tool-to-bone offset value. This value may be displayed as a numerical measurement 150 in a region of the display 28, 29. The system may operate to measure the tool-to-bone offset every time that the monitored motor operation deviates from a first level magnitude corresponding to the operation of the instrument in free space, that is, not in contact with the bone. This may include, for example, every time that the motor operation transitions from a first level magnitude to a second level magnitude corresponding to the motor operation while the tool is in contact with the bone, as is illustrated, for example at time $T_2$ in FIG. 6.

Because the value of the tool-to-bone offset may change over time as the surgical procedure progresses, the numerical measurement 150 may be a continuously updated value changing based on the most recent evaluation of the tool-to-bone offset. In addition, the historical data may be recorded and displayed so that the user can track and monitor trends in the tool-to-bone offset and be aware as the magnitude increases to a level where the navigation guidance cannot be relied upon to have a high level of accuracy and remedial action may be required. For example, as illustrated in FIG. 5B, a portion of the user interface 140 includes a graph of tool-to-bone offset values that tracks and displays the changing value over time. The graph 152 shows the current value at the right side of the graph, with the trend line 154 of past values scrolling toward the left side of the display. The illustration is not intended to be limited, and other graphical forms are contemplated without departing from the scope of the present disclosure.

Monitoring and displaying the tool-to-bone offset may present various ways of communicating the system status to the user. For example, the numerical measurement 150 may be displayed in different colors depending on the magnitude. A visual alert 144 may illuminate in different colors or blink in a varying frequency in order to alert the user of changing conditions. The system may be programmed with or may prompt the user to enter threshold values for the tool-to-bone offset to trigger different types of actions.

In one example, the tool-to-bone offset may be maintained less than 0.50 millimeters or else trigger a responsive action like disconnecting the instrument from power. It may be desirable to alert the user to a changing condition before it reaches that threshold. The numerical measurement 150 may be displayed in a first color for values between 0.00 millimeters and 0.25 millimeters. The numerical measurement 150 may be displayed in a second color, different from the first, for values between 0.25 millimeters up to 0.4 millimeters. The numerical measurement 150 may be displayed in a third color different from the first or second, for values greater than 0.4 millimeters. Likewise, the trend line may be displayed in different colors as the value changes. The first color may be green, the second yellow, and the third red. These illustrations are offered as examples and are not intended to be limiting.

In either the conditions of FIGS. 4A and 4B or 5A and 5B, the system may alert the user of an error condition and advise as to potential remedial action. The preferred remedial action may depend on the specific error encountered. In one example, if an error condition arises from a broken or worn tool, the remedial action would be to replace the tool. In another example, if an error condition arises from displacing a tracker from its relationship to the associated tracked object, or if the navigation cart assembly is jostled or bumped, re-registration of the trackers to the object in the localizer coordinate system may be the appropriate remedial action. These illustrations are only examples and are not intended to be limiting.

Figure 7:
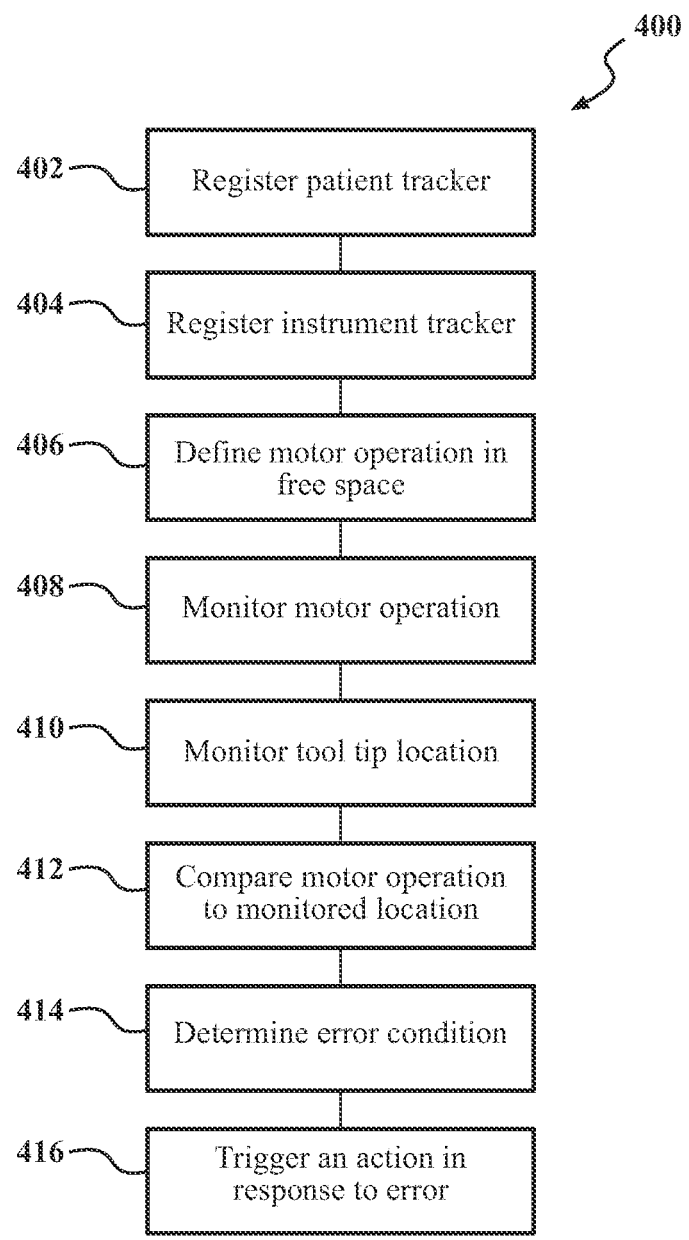
FIG. 7 is a flow chart illustrating a first method of navigating a surgical instrument relative to a bone.
Figure 8:
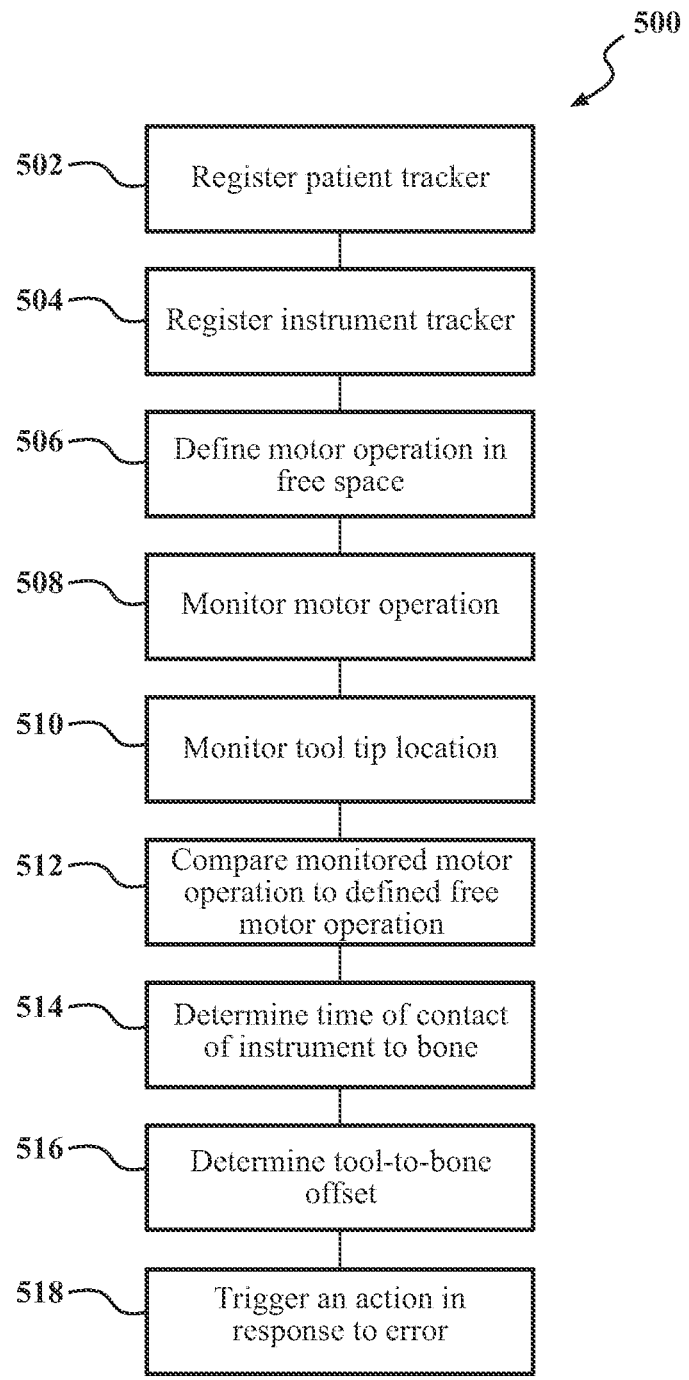
FIG. 8 is a flow chart illustrating a second method of navigating a surgical instrument relative to a bone and determining a tool-to-bone offset.

Illustrated in FIG. 7 is a first method 400 of navigating a surgical instrument having a variable speed motor relative to a bone. The method includes using the navigation system 20, which—as described above—includes a localizer having a localizer coordinate system, an instrument tracker coupled to the surgical instrument and a patient tracker coupled to the bone. The method uses a controller communicating with the navigation system and controlling the surgical instrument.

In a first step 402 of the method 400 shown in FIG. 4, the user registers the patient tracker to the bone. Registering the patient tracker relates the patient tracker coordinate system to the localizer coordinate system. This step also defines the location and orientation of the bone relative to the patient tracker so that the navigation system can track and monitor the position and orientation of the bone based on detected movement of the patient tracker and updating the virtual representation of the bone in the navigation system.

In a second step 404, the user registers the instrument tracker to the surgical instrument. Registering the instrument tracker relates the instrument tracker coordinate system to the localizer coordinate system. This step also defines the location and orientation of the instrument tool tip relative to the instrument tracker so that the navigation system can track and monitor the position and orientation of the instrument tool tip based on the detected movement of the instrument tracker and updating the virtual representation of the instrument in the navigation system.

The method includes at step 406, defining a motor operation for the surgical instrument or article when the tool tip is not in contact with the bone. This defining step can comprise evaluating at least one of the power, the voltage, the current, the rotational speed, or other operating parameter, or combination of parameters, that characterizes the operation of the motor. Data representing the operating parameter can be stored in a memory of the controller controlling the operation of the surgical instrument. Alternatively, or in addition, the data can be communicated by the controller to the navigation system. In a further alternative or addition, the data can be stored on a memory incorporated into the surgical instrument itself, or another device in communication with the instrument or console.

During a surgical operation and after an operating parameter is analyzed to define the motor operation in free space, the method includes the controller monitoring the motor operation of the instrument at step 408. This monitoring can comprise periodically receiving a signal indicating the motor operation and recording that signal as data representing the motor operation at the time the signal is received. In this way, the controller can create a record of the motor operation over time during the surgical operation.

Concurrently with monitoring the motor operation, the method includes monitoring the position of the instrument tool tip relative to the patient bone with the navigation system at step 410. The trackers mounted to the instrument and to the bone, respectively, are sensed by the navigation system, and based on the earlier registrations, the relative position of the tool tip and bone can be determined by the navigation system and, optionally, virtually represented on the displays. As part of monitoring the position of the tool tip and the bone, the navigation system can determine when contact is made between the instrument and the bone in the localizer coordinate system.

Upon determining that contact had been made between the instrument and the bone, the method includes, at step 412, comparing the motor operation to the monitored position of the instrument tool tip. The navigation system, in communication with the instrument controller, can evaluate the motor operation of the instrument. The evaluation considers whether the motor operation matches the defined motor operation for the instrument when the instrument tool tip is not in contact with the bone.

If the navigation system determines the instrument is in contact with the bone based on the tracked positions, and the motor operation indicates that the instrument is not in contact with the bone at that time, the method includes, at step 414, determining an error condition. This determination reflects that some disturbance or aberration has entered the system. The accuracy and reliability of the navigation system cannot be relied upon when the tracked locations in the navigation system do not reflect the true physical location of the instrument or bone.

Once an error condition is determined, the method includes, at step 416, triggering an action in response to determining the error condition so that appropriate remedial actions may be taken.

In one alternative, the method optionally includes defining a second motor operation for the instrument when the instrument tool tip is in contact with the bone. Similar to the first motor operation for the instrument when the instrument tool tip is not in contact with the bone, data representing the operating parameters of the second motor operation may comprise at least one of the power, the voltage, the current, the rotational speed, or other operating parameter, or combination of parameters, that characterizes the operation of the motor while in contact with the bone. This data representing the second motor operation can be stored in the memory of the controller controlling the operation of the surgical instrument. Alternatively, or in addition, the data can be communicated by the controller to the navigation system. In a further alternative or addition, the data can be stored on a memory incorporated into the surgical instrument itself.

Defining a second motor operation for when the surgical instrument is in contact with the bone, the method can include determining a second error condition when the monitored position of the instrument tool tip is not in contact with the bone in the localizer coordinate system but the motor operation is equal to the second defined motor operation—being the motor operation for when the instrument tool tip is in contact with the bone. Upon determining the second error condition is present, the method can include triggering a second action so that appropriate corrective action can be taken.

With regard to either error condition discussed above, the resulting action can include one or more of sounding an audible alert, displaying a visual alert, activating a tactile alert, cutting off power to the surgical instrument, or combinations thereof. Sounding an audible alert can include any kind of sound alarm, beep, buzzer or the like. Displaying a visual alert may include displaying a prompt on one or more of the displays of the navigation system that indicates the nature of the error condition determined. A visual alert may also include illuminating a light, such as an LED light on the surgical instrument itself. The visual alert may include any other visible type indication that an error condition has been determined. Activating a tactile alert may include energizing a vibratory feature of the instrument or the footswitch. The vibration may be characterized as a pattern of vibrations associated with the type of error so that the user can distinguish among different types of errors based on the type of vibration alone.

Illustrated in FIG. 5 is a second method 500 of navigating a surgical instrument having a variable speed motor relative to a bone and determining a tool-to-bone offset. The second method 500 is similar in some respects to the first method 400 described above. Steps of the second method 500 may be defined in relation to the steps of the first method 400 where such similarity exists. Specifically, the second method 500 employs a navigation system, surgical instrument, instrument tracker and patient tracker similar to the method 400. Likewise, a controller is in communication with the navigation system and provides power to the surgical instrument.

The second method 500 begins with the same steps 502, 504 of registering the patent tracker to the bone and the instrument tracker to the surgical instrument as steps 402 and 404. The second method 500, also includes the step 506, of defining a first motor operation for the surgical instrument while the instrument is not in contact with the bone, which is the same as step 406 described above. Further similar to the first method 400, the second method 500 includes the steps 508 and 510 of monitoring the motor operation with the controller and monitoring the position of the instrument tool tip relative to the bone with the navigation system, as in steps 408 and 410.

Deviating from the first method 400, the second method 500 includes comparing the monitored motor operation to the defined first motor operation at step 512. This comparison can be performed repeatedly over time on a continuous cycle at some frequency during the course of the operation. The second method 500 also includes determining, at step 514, as a result of the comparison at step 512, a contact time between the instrument tool tip and the bone when the monitored motor operation deviates from the defined first motor operation. When the continuously monitored characteristic of the motor operation changes from the defined first motor operation—representing the motor operation when the instrument is not in contact with the bone—the time of contact between the instrument and the bone can determined.

Once the time of contact between the instrument and the bone has been determined at step 514, the second method 500 includes, at step 516, determining with the navigation system, at the contact time, a tool-to-bone offset as a distance between the instrument tool tip and a surface of the bone in the localizer coordinate system. The navigation system monitoring the position of the instrument tool tip and the bone can receive a signal from the instrument controller indicating the contact between the tool tip and the bone, based on the determination by the controller that the monitored motor operation has deviated from the first defined motor operation when the instrument is not in contact with the bone.

Given the time of contact, the navigation system evaluates the tracked positions of the tool tip and the bone and computes a distance between the closest points of the tool tip and the surface of the bone in the localizer coordinate system, when the navigation system calculates that the tool tip is separated from the bone. In another case, the navigation system may calculate that the tool tip is penetrating into the bone by some distance given the time of contact based on the controller determining a deviation from the defined motor operation. In this case, the navigation system computes a distance normal to the surface of the bone of the maximum penetration depth of any point of the tool tip. In either case, the calculated distance is the tool-to-bone offset. Said differently, the tool-to-bone offset is a measure of the margin of accuracy between the true physical position of the tool relative to the bone and the virtual representations of the position of the tool relative to the bone.

As described above, there are a number of factors that can introduce or increase a tool-to-bone offset. If a tracker is displaced or deformed after it has been registered, it can lead to a decrease in the navigation accuracy. Likewise, if the navigation cart assembly is jostled or bumped during the operation, causing the camera unit to shift, that can also lead to a decrease in the navigation accuracy. Other factors can include tool wear, tool deformation, or gross removal of tissue from the bone. It is preferable to maintain a low tool-to-bone offset in maintaining a consistent and highly accurate navigation.

If the tool-to-bone offset increases too high, the accuracy of the navigation guidance may be compromised and require remedial action. The second method 500 therefor includes the step 518 of triggering an action when the tool-to-bone offset exceeds a predefined magnitude. In one example, the predefined magnitude is 0.5 millimeters. That is, when the instrument contacts the bone, as determined by a deviation in the motor operation monitored by the controller, the navigation system calculates that the tool tip is 0.5 millimeters from the surface of the bone. Although described with reference to a specific magnitude, this is not intended to be limiting, and other limits are contemplated. Moreover, different limits may be applicable to different tools or different applications of the same tool. This step 518 of triggering an action is similar to the step 416 of triggering an action in response to determining an error condition. The resulting action can include one or more of sounding an audible alert, displaying a visual alert, activating a tactile alert, cutting off power to the surgical instrument, or combinations thereof, as described above.

In order to provide information to the user, the second method 500 may further include the step of displaying on a display of the navigation system the value of the tool-to-bone offset. This can allow the user to track and monitor the accuracy of the navigation guidance being provided by the navigation system. In implementing this method in a surgical operation, the step of determining the value of the tool-to-bone offset may be repeated multiple times throughout the procedure, for example, each time the controller determines a time of contact between the instrument and the bone based on a deviation in the motor operation. Thus, the display of the tool-to-bone offset may be a continuously updated value for each time the determination is performed. In addition to a numerical presentation of the value of the tool-to-bone offset, this information may also, or alternatively, be displayed as a chart, or line graph, of values over time.

To further assist the user, the value of the tool-to-bone offset may be displayed differently based on the magnitude.

For example, lower magnitudes, indicating a low tool-to-bone offset and a high degree of accuracy in the navigation guidance, may be displayed in a first color, whereas higher magnitudes may be displayed in a second color, different from the first color. Yet further, even higher magnitudes may be displayed in a third color, different from the first and the second colors. Other color combinations or visual representations may also be employed in this same way.

To facilitate this dynamic display of the tool-to-bone offset value, the second method 500 may include the step of defining a first level magnitude and a second level magnitude. These first and second level magnitudes may be predefined in the system as default values. Alternatively, the first and second level magnitudes may be entered by the user at the start of the operation or during a set up operation of the system. In one example, the first level magnitude may be 0.25 millimeters and the second level magnitude may be 0.4 millimeters.

In one example, when the tool-to-bone offset is calculated to be less than the first level magnitude, the displayed value may be presented in a green color. When the tool-to-bone offset is calculated to be less than the second level magnitude, the displayed value may be presented in a yellow color. When the tool-to-bone offset is above the second level magnitude the displayed value may be presented in a red color. These color designations are not intended to be limiting and are only intended to illustrate one example. In another case, the dynamic display of the tool-to-bone offset may utilize variable size, in the alternative or in addition to changing the color of the displayed value.

The first and second level magnitudes of the tool-to-bone offset value may also be utilized for triggering one or more of the actions at step 518 of the second method 500. For example, upon the tool-to-bone offset reaching or exceeding the first level magnitude a visual alert may be triggered, and upon the tool-to-bone offset reaching or exceeding the second level magnitude, a combination of visual and audible alerts may be triggered.

Additionally, a third level magnitude may also be defined in the same or a different manner as the first and second level magnitudes. The third level magnitude may represent the value of the tool-to-bone offset where the system determines to disable power from the controller to surgical instrument. When the tool-to-bone offset reaches the third level magnitude, the accuracy of the navigation system may be compromised to the point that risk of harm is present and so the surgical instrument must be disabled until remedial action is taken.

As described above, the navigation system may alert the user to a condition where remedial action is required to improve the accuracy of the navigation guidance in response to certain errors or to determined values of the tool-to-bone offset. There are a number of different remedial actions that are possible, and the proper correction may depend on the specific error encountered. In one example, if an error condition arises from a broken or worn tool, the remedial action would be to replace the tool. In another example, if an error condition arises from displacing a tracker from its relationship to the associated tracked object, or if the navigation cart assembly is jostled or bumped, re-registration of the trackers to the object in the localizer coordinate system may be appropriate remedial action.

In another example, in a surgical operation where a substantial amount of tissue is removed, the virtual representation of the anatomy will no longer represent the patient's actual anatomy. To remedy this situation, additional imaging, modeling, and registration may be necessary to redefine the location of tissue surfaces within the virtual representation of the anatomy. In one example, the surgical instrument may be unpowered and used as a pointer to touch off of multiple points on the resected surface of the anatomy to create a new point cloud for the navigation system to redefine the surface of the virtual representation of the bone.

The disclosed methods may be practiced with an improved surgical system, as shown in FIGS. 1 and 2, and described above in various configurations. The surgical system comprises a surgical instrument having a variable speed motor and a tool tip. The surgical instrument is in operative communication with a controller for providing power to the surgical instrument. The controller is further operable to monitor a motor operation of the instrument and comprises a processor and a memory operable to store information, including information representing the monitored motor operation. The system also comprises an instrument tracker coupled to the instrument and a patient tracker to be coupled to a patient's anatomy.

The surgical system also comprises a navigation system. The navigation system includes a localizer and a navigation computer. The navigation computer includes a processor and a memory to store information, including information representing the surgical instrument, and information representing the patient's anatomy, in a virtual space and relative to a localizer coordinate system within the virtual space. The navigation system is operable to track the location of the instrument and the bone in virtual space during the operation based on information gathered by the localizer. The localizer is operable to register the location of the instrument tracker and the location of the patient tracker relative to a localizer coordinate system and to gather information about the location of the instrument and the bone in cooperation with the instrument tracker and the patient tracker respectively.

The controller and the navigation system are in electronic communication and configured to cooperate with each other. In operation, the controller and the navigation system determine a time of contact between the tool tip and the bone based on a change in the motor operation of the instrument. The controller and the navigation system also determine, at the time of contact, a tool-to-bone offset as a distance between the tracked location of the tool top and the tracked location of the bone.

The surgical system may further comprise an alert device. The controller and the navigation system are in further communication with the alert device and operate to trigger an action when the tool-to-bone offset is greater than a predefined magnitude. The alert device may include a visual alert device such as lights or displays on the console 82, the computer cart assembly 24, on the camera unit 36, or elsewhere in the operating environment. Other visual alerts may take the form of prompts for user action, information displays, or other shapes, forms, pictures or otherwise. The alert device may include an audible alert device such as a speaker, bell, horn, buzzer or the like. Other audible alerts may include tones, alarms, prerecorded messages or otherwise. The alert device may include a haptic alert device capable of generating a tactile alert perceptible to the user, such as through vibration.

In a configuration where trackers are properly registered to the surgical instrument and to the patient's anatomy, a user may place an unpowered tool tip of the surgical instrument in contact with the patient's anatomy, and the navigation system will correctly determine that the tool tip is in contact with the patient's anatomy in the common coordinate system, without any gap or overlap. However, it is possible for the trackers, the surgical instrument, or the anatomy to deflect or deform, or the camera unit of the navigation system to be disturbed, in a way the causes the registration to become inaccurate. Therefore, it is desirable to provide a method for the navigation system to perform a registration verification operation that does not require the tool to be powered and thus does not rely on any parameter of the tool operating in free space or in contact with a patient's anatomy. The user may place the tool tip of the surgical instrument in stationary contact with the patient's anatomy, in an unpowered state so that the anatomy is not affected by the tool and hold that position to trigger the navigation system to perform a registration verification.

Figure 9:
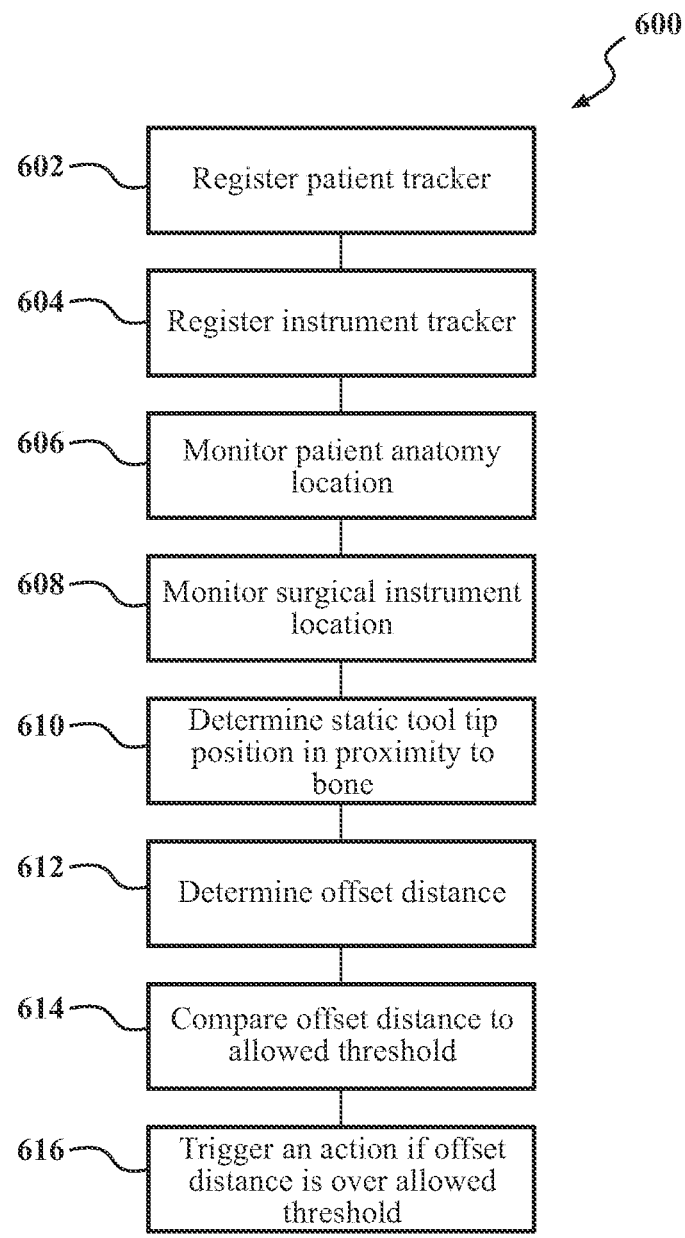
FIG. 9 is a flow chart illustrating a method of performing a tracking registration verification.

Illustrated in FIG. 9, a method 600 of operating a surgical navigation system during a surgical operation to verify a tracking registration is provided. In the method 600, the surgical navigation system, as described above, includes a localizer having a localizer coordinate system, an instrument tracker coupled to the surgical instrument, and a patient tracker coupled to the patient's anatomy—for example, a vertebra, other bone, or soft tissue. References to a patient's anatomy, a specific bone, or bone in general, should be read broadly to include soft tissue and other non-bone applications. The method 600 uses a controller communicating with the navigation system and controlling the surgical instrument.

In a first step 602 of the method 600, the user registers the patient tracker to the bone. Registering the patient tracker relates the patient tracker coordinate system to the localizer coordinate system or other common coordinate system. This step also defines the location and the orientation of the bone relative to the patient tracker so that the navigation system can track and monitor the position and orientation, or pose, of the bone based on the detected movement of the patient tracker and updating the virtual representation of the anatomy in the navigation system.

In a second step 604 of the method 600, the user registers the instrument tracker to the surgical instrument. Registering the instrument tracker relates the instrument tracker coordinate system to the localizer coordinate system or other common coordinate system. This step 604 also defines the position and orientation of the instrument tool tip relative to the instrument tracker so that the navigation system can track and monitor the position and orientation, or pose, of the instrument tool tip based on the detected movement of the instrument tracker and updating the virtual representation of the instrument in the navigation system.

The method 600 includes the steps 606, 608 of monitoring, with the navigation system, the pose of the anatomy and the location of the surgical instrument over time and tracking the pose of the anatomy and the instrument with a virtual representation which can be displayed to the user. Monitoring the location of the patient's anatomy and the surgical instrument includes monitoring both the position and orientation of the tracked objects. The position and orientation are monitored over time on a continuous cycle at a frequency during the course of the operation. With this information, the navigation system can determine velocity, acceleration, and other quantities, including magnitude and direction of motion in the common coordinate system, and relative to other tracked objects.

The method 600 includes the step 610 of determining that the tool tip of the surgical instrument is statically positioned within a predefined proximity to the patient's anatomy. In this step, the navigation system monitors the velocity of the tool tip relative to the anatomy, in addition to monitoring the position of the tool tip and of the anatomy. During operation, the user places the tool tip in contact with the bone, while the tool is not powered, in order to prompt the navigation system to verify the registration of the trackers on the surgical instrument and patient's anatomy.

Because the registration is susceptible to error, the navigation system may evaluate the registration verification when the tool tip is determined by the navigation system to be stationary within a predefined proximity with the patient's anatomy. The navigation system may determine that the tool tip is stationary when the tracked position does not change for a predetermined period of time. The predetermined period of time may be preprogrammed to the navigation system to be, for example, three seconds, five seconds, or other duration. The predefined proximity may be, for example, about 3 millimeters, about 1 millimeter, or about 0.5 millimeter. The predefined proximity may be some other distance value suitable to the level of precision measurable by the navigation system. During a configuration of the navigation system, such as during start up prior to the surgical operation, a user may be prompted to select a duration for the predetermined period of time or a distance for the predefined proximity from a list of options, or else may be prompted to enter a duration or distance through a touch pad, button selection, touchscreen or other input.

The navigation system may determine that the tool tip is stationary when the tracked position and orientation of the tool tip is static and does not change during the predetermined period of time. Alternatively, the position may be determined to be stationary when the position and orientation does not change by more than a specific magnitude. Further alternatively, the position may be determined to be stationary when the position and orientation does not change, or else does not change by more than a specific magnitude in a specific direction, such as where the specific direction is in the direction toward the anatomy.

Once the navigation system determines that the tool tip is stationary in a static position and orientation in proximity to the bone, the method 600 includes the step 612 of determining an offset distance. The offset distance is a measure of the inaccuracy in the system. The navigation system receives the input from the user indicating that the tool tip is in static contact with the anatomy and evaluates the tracked positions of the instrument tool tip and the patient's anatomy. The result of this evaluation, based on the tracked positions, may calculate that the tool tip is separated from the bone by a distance, or may calculate that the tool tip is penetrating into the bone by a distance, based on the tracked positions and orientations of the virtual representations of the surgical instrument and the patient's anatomy. The magnitude of the calculated distance defines a tool-to-bone offset and indicates the margin of accuracy between the true physical position of the tool tip relative to the anatomy and the virtual representations of the tool tip relative to the anatomy in the navigation system.

In calculating the offset distance, the navigation system identifies a first point on the virtual representation of the surgical instrument that is either the closest proximal point to the virtual representation of the patient's anatomy, or else is the point of deepest penetration or overlap of the virtual representation of the surgical instrument into the virtual representation of the patient's anatomy. Where the first identified point of the instrument is outside the anatomy, the offset distance is the shortest distance between the first identified point and some point on the surface of the virtual representation of the anatomy such that the offset distance is normal to the surface and directed outward. Where the first identified point of the instrument is internal to the virtual representation of the anatomy, the offset distance is the greatest distance between the first identified point and some point on the surface of the virtual representation of the anatomy such that the offset distance is normal to the surface and directed inward.

Once an offset distance is determined, the navigation system in the method 600, at step 614 compares the calculated offset distance to a predefined threshold for allowable system inaccuracy. If the offset distance is greater than the predefined threshold, indicating a lower level of accuracy than desired, the navigation system may be configured to trigger an action in response. In one example, the predefined threshold is 0.5 millimeters. That is, when the tool tip is in static contact with the anatomy, as determined by navigation system based on the tracked positions, the navigation system calculates that the virtual representation of the tool tip is 0.5 millimeters from the virtual representation of the anatomy. Although described with reference to a specific magnitude, this is not intended to be limiting, and other limits are contemplated. Moreover, different limits may be applicable to different tools or different applications of the same tool. The triggered action can include one or more of sounding an audible alert, displaying a visual alert, activating a tactile alert, disabling power to the surgical instrument, or combinations thereof, and as described above.

The predefined threshold may include multiple values indicating different levels of accuracy, where different actions are triggered depending on how the offset distance compares with the different values. For example, the predefined threshold may include a first predefined threshold and a second predefined threshold. Triggering an action may include triggering a first action when the offset distance is greater than the first predefined threshold and triggering a second action when the offset distance is greater than the second predefined threshold. The actions may include any action as described above to include audible alerts, visual alerts, tactile alerts, or various combinations thereof.

Figure 10:
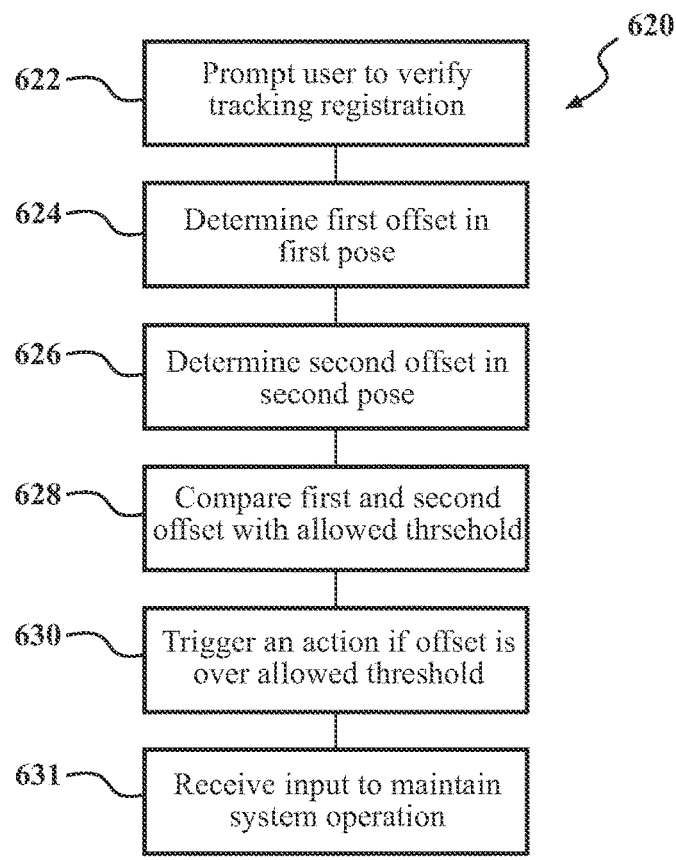
FIG. 10 is a flow chart illustrating a second method of performing a tracking registration verification.

The method 600 illustrated in FIG. 9, may be expanded as illustrated in FIG. 10 as method 620. In one expansion, the navigation system, at step 622, may prompt the user to initiate a registration verification cycle as detailed in method 600 above. The prompt may be presented to the user as a visual prompt, such as by showing a message on a display. Alternatively, a visual prompt may include a flashing light, or otherwise. The prompt may be presented to the user as an audible prompt, such as by a tone, beep, prerecorded message, or the like. The prompt may be presented as a haptic prompt, such as by a prescribed series or cycle of vibrations. The prompt may be presented to the user as a combination of visual, audible, or haptic prompts.

The method 620 includes step 624 of determining a first offset with the surgical instrument in a first pose. This step is performed consistent with the steps of method 600, shown in FIG. 9, with the static position of the tool tip comprising the first pose—position and orientation of the surgical instrument. The method 620 includes step 626 of determining a second offset in a second pose. This requires changing the position, orientation, or both, of the surgical instrument and placing the tool tip in static contact with the anatomy a second time. With the tool tip in static contact with the anatomy in a second pose, the navigation system determines a second offset value. The navigation system may therefore evaluate the tool-to-bone offset in this way from more than one angle to ensure the accuracy of the system in multiple angles.

Having determined first and second offsets from the first and second poses respectively in steps 624, 626, the navigation system compares the first and second offsets with an allowed threshold at step 628. In this step, the navigation system may independently compare the first offset with the allowed threshold and compare the second offset with the allowed threshold and may trigger an action if either one or the other of the first and second offsets are over the allowed threshold. The step 630 of triggering an action may be similar to step 616 of triggering an action.

Once an action is triggered in response to the navigation system determining that an offset is over an allowed threshold, the user may have the opportunity to enter an input to maintain system operation without taking other corrective action such as re-registering the trackers to the surgical instrument or to the patient's anatomy. The navigation system may receive an input to override or cancel the action triggered by the offset being greater than the allowed threshold at step 631. The navigation system may receive an input, such as a voice command, a gesture input, or other input through a keypad, touchscreen, or the like. Receiving the input to override or cancel the triggered action, the navigation system, and the surgical instrument, may return to normal operation.

Figure 11:
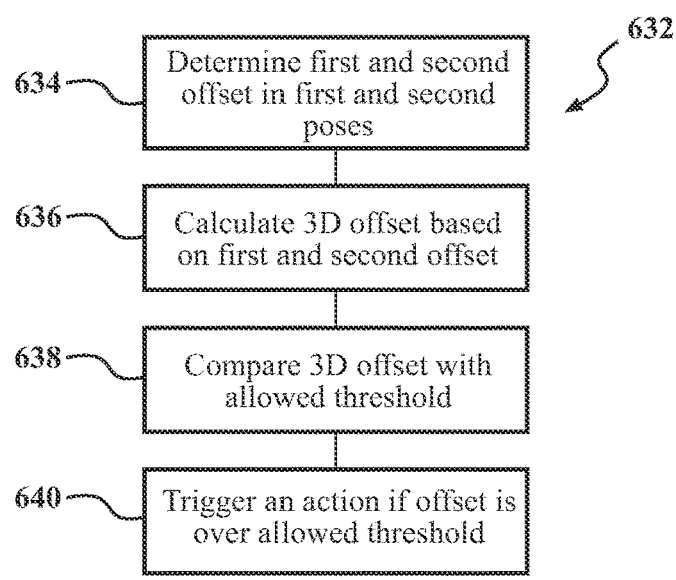
FIG. 11 is a flow chart illustrating additional steps for performing the tracking registration verification.

FIG. 11 illustrates method 632 as an alternative, or an addition, to step 628 of method 620 of comparing the first and second offsets to an allowed threshold. Once the navigation system has determined the first and second offsets in first and second poses, as in step 634, the navigation system may calculate a three-dimensional offset based on the first and second offsets and on the geometric relationship between the first and second poses, or more specifically, on the geometric relationship between the specific points of contact on the surface of the tool tip applied in static contact with the anatomy in the first and second poses. Once the three-dimensional offset value is determined, the navigation system may compare the three-dimensional offset with an allowed threshold, at step 638. The allowed threshold may be the same magnitude or a different magnitude as compared to the allowed threshold when comparing one of the first or second offsets. If the offset is over the allowed threshold, the method includes triggering an action at step 640.

As a further alternative, the methods 620 and 632, may additionally include determining a third offset in a third pose. In step 628 of method 620, comparing the first and second offset with an allowed threshold may include comparing the third offset with the allowed threshold. Likewise, in method 632, step 634 may include determining a third offset in a third pose in addition to determining the first and second offsets in the first and second poses. Further, in step 636, the navigation system may calculate the three-dimensional offset based on the first, second, and third offsets and the geometric relationships between the first, second and third poses, or first, second and third points of contact between the tool tip and the anatomy in the first, second, and third poses.

Figure 12:
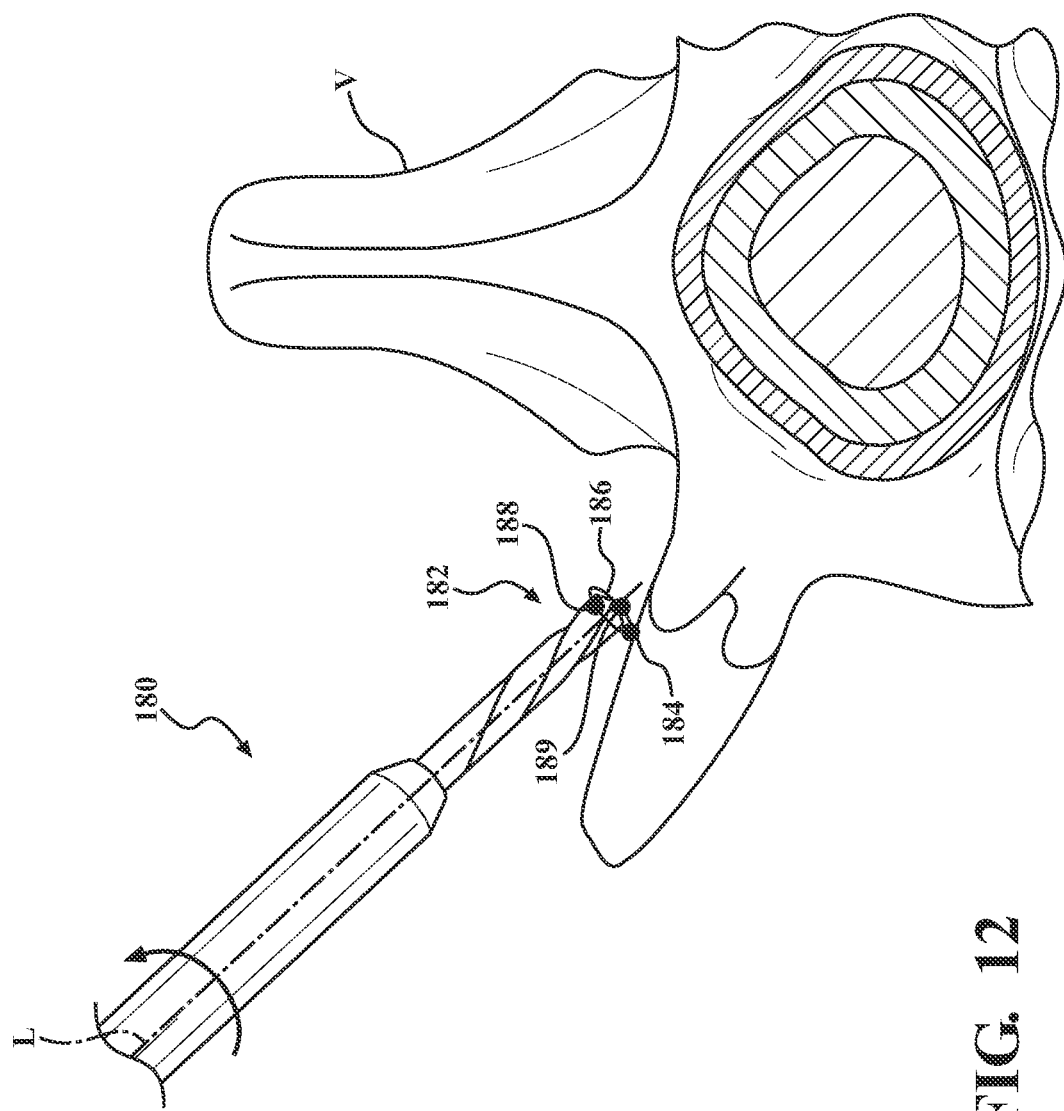
FIG. 12 shows a surgical instrument having an elongated aspect in contact with a bone.

Calculating the three-dimensional offset depends on the geometry of the tool tip. In a first example, as illustrated in FIG. 12, the tool tip 180 may include a substantially cylindrical, tapered, rounded-conical, or elongated aspect 182, such as with a drill bit or router. The elongated aspect 182 of the tool tip 180 may define a longitudinal axis L extending through a center and parallel with the elongated aspect 182. When placed in static contact with the anatomy, such as vertebra V, for verifying the registration and determining an offset value, the point of contact 184 between the tool tip 180 and the anatomy V is, for example, along the peripheral edge 186 at the end of the elongated aspect 182 at a distance from the longitudinal axis equal to the radius of the elongated aspect.

Figure 13:
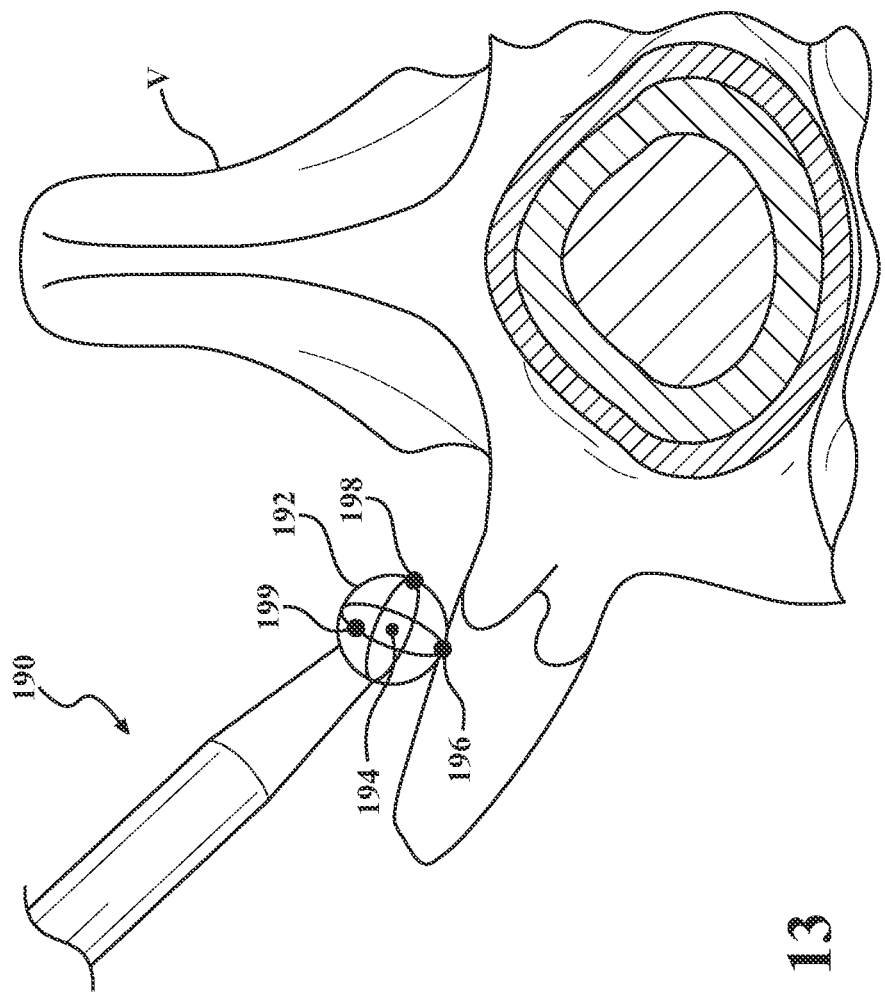
FIG. 13 shows a surgical instrument having a spherical aspect in contact with a bone.

In another example, as illustrated in FIG. 13, the tool tip 190 may include a substantially spherical aspect 192, such as with a round bur. The spherical aspect 192 of the tool tip 190 may define a centerpoint 194 at the center of the spherical aspect. When placed in static contact with the anatomy, such as a vertebra V for verifying the registration and determining an offset value, the point of contact 196 between the tool tip 190 and the anatomy V is, for example, on the surface of the spherical aspect 192 at a distance from the centerpoint 194 equal to the radius of the spherical aspect 192.

Determining a three-dimensional offset, such as at step 636 of the method 632, illustrated in FIG. 11, requires determining a first offset with the surgical instrument at a first pose with respect to the anatomy, a second offset at a second pose, and optionally, a third offset at a third pose. Placing the surgical instrument in multiple different poses presents a different view of the surgical instrument tracker to the camera unit of the localizer. The multiple views ensure that any registration error is able to be discerned by the navigation system and is not concealed by a particular view of the instrument.

To ensure sufficient differentiation in the views of the surgical instrument by the navigation system, there should be sufficient rotation of the surgical instrument from one pose to the next. For example, establishing a first offset distance at a first pose, the surgical instrument may be rotated so that the point of contact on the tool tip is about 90° away in the second pose from the point of contact on the tool tip in the first pose. As illustrated in FIG. 12, where the tool tip 180 has an elongated aspect 182, the second point of contact 188 may be about 90° from the first point of contact 184 via a rotation about the longitudinal axis L of the tool tip 180. As illustrated in FIG. 13, where the tool tip 190 has a spherical aspect 192, the second point of contact 198 may be about 90° from the first point of contact 196 via a rotation about the centerpoint 194 in any plane. Where a third offset distance is determined, a third point of contact 189, 199 in the third pose may be about 90° away from the first 184, 196 and the second 188, 198 points of contact in the first and second poses, respectively.

During the course of a surgical operation, the surgical instrument may be applied in contact with more than one bone, such as multiple vertebrae along a spine. At an initial phase of the surgical operation, trackers may be registered to each of the individual bones that will be affected by the operation. Transitioning from operating on one bone to operating on a second bone, a user may verify the registration of the tracker of the second bone following completion of the surgical intervention on the first bone. The user can trigger the navigation system to verify the tracking registration process by positioning the tool tip in static contact with the second bone. Alternatively, the navigation system, upon completion of a phase of the surgical plan applied to the first bone, may prompt the user to verify the registration before beginning the surgical intervention according to a surgical plan for the second bone.

The navigation system may designate a portion of the bone to contact with the tool tip for the registration verification. The portion of the bone designated for the registration verification may be an exposed portion of the bone that nonetheless is not targeted for resection according to the surgical plan. Selecting a portion not targeted for surgical intervention increases the likelihood that the bone surfaces match the virtual representation of the patient's anatomy to provide an accurate basis for verifying the tracker registration. The navigation system may display a graphical representation of the patient's anatomy with a particular portion highlighted, flagged, indicated with an arrow, outline, or other signifier to identify the portion of the anatomy to the user.

The above description is provided in an illustrative manner. It is to be understood that the terminology which has been used is intended to be in the nature of words of description rather than of limitation. Many modifications and variations are possible in light of the above teachings. Therefore, within the scope of the appended claims, features or implementations may be practiced other than as specifically described.

CLAUSES

I. A surgical system comprising:
    a surgical instrument having a variable speed motor and a tool tip;
    a controller for providing power to the surgical instrument, the controller operable to monitor a motor operation of the instrument, the controller comprising a processor and a memory, the memory operable to store information, including information representing the motor operation of the instrument;
    an instrument tracker coupled to the instrument;
    a patient tracker to be coupled to a bone; and
    a navigation system comprising a localizer;
        the navigation system operable to store information representing the surgical instrument, and information representing the bone, in a virtual space;
        the localizer operable to register a location of the instrument tracker and a location of the patient tracker relative to a localizer coordinate system, and to gather information about the location of the instrument and the bone in cooperation with the instrument tracker and the patient tracker, respectively;
        the navigation system operable to track the location of the instrument and the location of the bone in the virtual space based on information gathered by the localizer;
    wherein the controller and the navigation system are in electronic communication and configured to cooperate to:
        determine, based on a change in the motor operation, a time of contact between the tool tip and the bone; and
        determine, at the time of contact, a tool-to-bone offset as a distance between the tracked location of the tool tip and the tracked location of the bone.

II. The surgical system of clause I, wherein monitoring the motor operation comprises one of monitoring a power level, a voltage level, a current level, or combinations thereof, and wherein the motor operation comprises a first motor operation when operated while the tool tip is not in contact with bone and a second motor operation, different from the first motor operation, when operated while the tool tip is in contact with bone.

III. The surgical system of any of clauses I-II, further comprising an alert device, wherein the controller and the navigation system are further configured to trigger an action when the tool-to-bone offset is greater than a predefined magnitude.

IV. The surgical system of clause III, wherein triggering the action comprises one of sounding an audible alert, displaying a visible alert, activating a tactile alter, cutting off power to the surgical instruments, or combinations thereof.

V. The surgical system of any of clauses III-IV, wherein the predefined magnitude is 0.5 millimeters.

VI. The surgical system of any of clauses III-V, wherein the predefined magnitude comprises a first predefined magnitude and a second predefined magnitude, different from the first predefined magnitude, and wherein the controller and the navigation system are configured to trigger a first action when the tool-to-bone offset is greater than a first predefined magnitude and a second action, different from the first action when the tool-to-bone offset is greater than a second predefined magnitude.

VII. The surgical system of any of clauses I-VI, wherein the controller and the navigation system are configured to cooperate to determine each occurrence of a change in motor operation during a medical procedure; determine a time of contact for each occurrence of the change in motor operation; determine, for each time of contact, a tool-to-bone offset; and log a series of determined tool-to-bone offsets.

VIII. The surgical system of any of clauses I-VI, further comprising a display device in electronic communication with one of the controller, the navigation system, or the combination of the controller and the navigation system, and wherein the controller, the navigation system or the combination of the controller and the navigation system are further configured to cause the display device to display the determined tool-to-bone offset.

IX. The surgical system of clause VIII, wherein the controller, the navigation system or the combination of the controller and the navigation system are further configured to cause the display device to display the series of determined too-to-bone offsets as a serially updating value.

X. A surgical system comprising:
  a surgical instrument having an actuator and a tool tip;
  a controller for providing power to the surgical instrument, the controller operable to monitor an actuator operation of the instrument, the controller comprising a processor and a memory, the memory operable to store information, including information representing an actuator operation of the instrument;
  an instrument tracker coupled to the instrument;
  a patient tracker to be coupled to a tissue;
  a navigation system comprising a localizer;
    the navigation system operable to store information representing the surgical instrument, and information representing the tissue, in a virtual space;
    the localizer operable to register a location of the instrument tracker and a location of the patient tracker relative to a localizer coordinate system, and to gather information about the location of the instrument and the tissue in cooperation with the instrument tracker and the patient tracker, respectively;
    the navigation system operable to track the location of the instrument and the location of the tissue in the virtual space during operation based on information gathered by the localizer;
  wherein the controller and the navigation system are in electronic communication and configured to cooperate to:
    determine, based on a change in the actuator operation, a time of contact between the tool tip and the tissue; and
    determine, at the time of contact, a tool-to-bone offset as a distance between the tracked location of the tool tip and the tracked location of the tissue.

XI. A surgical system comprising:
  a navigation system comprising a control console and a localizer;
    the navigation system in communication with first data representing a surgical instrument, the surgical instrument including a tool tip, and second data representing a patient's anatomy;
    the navigation system operable to track the surgical instrument and the anatomy in a virtual space during a surgical operation based on information gathered by the localizer from an instrument tracker coupled to the surgical instrument and a patient tracker coupled to the anatomy;
    wherein the navigation system is configured to:
      track the surgical instrument and the anatomy and store data representing the tracked surgical instrument pose and the anatomy pose in a common coordinate system;
      determine the tool tip is within a predefined proximity to the anatomy based on the tracked surgical instrument pose and the tracked anatomy pose;
      determine the tool tip does not depart the predefined proximity by more than a predefined magnitude over a predefined duration;
      determine an offset distance based on the tracked surgical instrument and the tracked anatomy in the common coordinate system; and
      compare the offset distance to a predefined threshold.

XII. The surgical system of clause XXI, further comprising an alert device, wherein the navigation system is further configured to trigger an action when the offset distance is greater than the predefined threshold.

XIII. The surgical system of clause XII, wherein the alert device is a footswitch, wherein the footswitch is operable to generate a vibration; and wherein the action is a vibration of the footswitch.

XIV. The surgical system of clause XII, wherein the action comprises one of sounding an audible alert, displaying a visible alert, activating a tactile alter, cutting off power to the surgical instrument, or combinations thereof.

XV. The surgical system of any of clauses XII-XIV, wherein the predefined threshold is 0.5 millimeters.

XVI. The surgical system of any of clauses XII-XIV, wherein the predefined magnitude comprises a first predefined magnitude and a second predefined magnitude, different from the first predefined magnitude, and wherein the navigation system is configured to trigger a first action when the offset distance is greater than a first predefined magnitude and a second action, different from the first action when the offset distance is greater than a second predefined magnitude.

XVII. The surgical system of any of clauses XII-XVI, further comprising a display device in electronic communication with the navigation system, and wherein the navigation system is further configured to cause the display device to display the determined offset distance.

XVIII. The surgical system of clause XVII, wherein the offset distance is displayed in a first color when the offset distance if less than the predefined threshold and is displayed in a second color, different from the first color, when the offset distance is greater than the predefined threshold.

XIX. A method of performing a surgical operation, the method comprising:
  coupling a patient tracker to a patient's anatomy;
  coupling an instrument tracker to a surgical instrument, the surgical instrument including a tool tip;

operating a navigation system to register the instrument tracker and the patient tracker in a common coordinate system and to track the surgical instrument and the patient's anatomy;
pausing the tool tip in contact with the anatomy for a predefined duration to initiate a registration verification;
wherein the navigation system is configured to determine an offset distance based on the tracked surgical instrument and the tracked patient's anatomy; and
evaluating the offset distance against a predefined threshold.

XX. The method of clause XIX, wherein the navigation system is configured to trigger an action when the offset distance is greater than the predefined threshold, wherein the action includes one of sounding an audible alert, displaying a visual alert, activating a tactile alert, cutting off power to the surgical instrument or combinations thereof.

XXI. The method of clause XX, further comprising providing an input to the navigation system to terminate the triggered action.

XXII. The method of clause XIX, wherein the patient's anatomy includes a first bone and a second bone; the method further comprising:
operating the surgical instrument in application to the first bone;
operating the surgical instrument in application to the second bone; and
wherein pausing the tool to initiate a registration verification is performed in contact with the second bone subsequent to operating the surgical instrument in application to the first bone and prior to operating the surgical instrument in application to the second bone.

What is claimed is:

1. A method of navigating a surgical instrument having a variable speed motor relative to a bone, the method using a navigation system including a localizer having a localizer coordinate system, an instrument tracker coupled to the surgical instrument, a patient tracker coupled to a bone, and a controller in communication with the navigation system, the controller controlling the surgical instrument, the method comprising:
registering, with the localizer, the patient tracker in the localizer coordinate system, defining a bone location of the bone relative to the localizer coordinate system;
registering, with the localizer, the instrument tracker in the localizer coordinate system, defining an instrument location of an instrument tool tip relative to the localizer coordinate system;
defining a motor operation for the instrument when the instrument tool tip is not in contact with the bone;
monitoring, with the controller, motor operation of the instrument during a medical procedure;
monitoring, with the navigation system, a position of the instrument tool tip relative to the bone to determine when the instrument tool tip is in contact with the bone in the localizer coordinate system;
comparing the motor operation to the monitored position of the instrument tool tip;
determining an error condition when the monitored position of the instrument tool tip is in contact with the bone in the localizer coordinate system and the monitored motor operation equals the defined motor operation for the instrument when the instrument tool tip is not in contact with the bone; and
triggering an action when an error condition is determined.

2. The method of claim 1, wherein defining the motor operation for the instrument when the tool tip is not in contact with the bone comprises defining a threshold value for power, voltage, current, or combinations thereof, when the motor is operated while the instrument tool tip is not in contact with the bone.

3. The method of claim 1, further comprising defining a second motor operation for the instrument when the instrument tool tip is in contact with the bone; determining a second error condition when the monitored position of the instrument tool tip is not in contact with the bone in the localizer coordinate system and the monitored motor operation equals the second defined motor operation for the instrument when the instrument tool tip is in contact with the bone; and triggering a second action when the second error condition is determined.

4. The method of claim 3, wherein triggering one of an action or a second action comprises one of sounding an audible alert, displaying a visual alert, activating a tactile alert, cutting off power to the surgical instrument, or combinations thereof.

5. A method of navigating a surgical instrument having a variable speed motor using a navigation system including a localizer having a localizer coordinate system, an instrument tracker coupled to the surgical instrument, a patient tracker coupled to a bone, and a controller in communication with the navigation system and providing power to the surgical instrument, the method comprising:
registering, with the localizer, the patient tracker in the localizer coordinate system, defining a bone location of the bone relative to the localizer coordinate system;
registering, with the localizer, the instrument tracker in the localizer coordinate system, defining an instrument location of an instrument tool tip relative to the localizer coordinate system;
defining a first motor operation of the surgical instrument operating while not in contact with the bone;
monitoring, with the controller, a motor operation of the surgical instrument during a medical procedure;
monitoring, with the navigation system, a position of the instrument tool tip relative to the bone in the localizer coordinate system;
comparing the monitored motor operation to the defined first motor operation;
determining a contact time between the instrument tool tip and the bone when the monitored motor operation deviates from the defined first motor operation;
determining, with the navigation system at the contact time, a tool-to-bone offset as a distance between the instrument tool tip and a surface of the bone in the localizer coordinate system; and
triggering an action when the tool-to-bone offset exceeds a predefined magnitude.

6. The method of claim 5, wherein triggering an action comprises one of sounding an audible alert, displaying a visual alert, activating a tactile alert, cutting off power to the surgical instrument, or combinations thereof.

7. The method of claim 5, wherein the predefined magnitude is 0.5 millimeters.

8. The method of claim 5, further comprising displaying, on a display device, the determined tool-to-bone offset.

9. The method of claim 8, wherein monitoring the position of the instrument tool tip relative to the bone comprises tracking the instrument location of the instrument tool tip and the bone location of the bone during the medical procedure; the method further comprising detecting, with the navigation system, each occurrence during the medical procedure of the monitored position of the instrument tool tip being in contact with the surface of the bone and logging a series of tool-to-bone offset values determined during the medical procedure upon each occurrence.

10. The method of claim 9, further comprising displaying, on a display device, the series of tool-to-bone offset values as one of a serially updating value, a chart of tool-to-bone offsets over time, or combinations thereof.

11. The method of claim 8, further comprising defining a first level magnitude and a second level magnitude, wherein the step of displaying the determined tool-to-bone offset comprises displaying the determined tool-to-bone offset in a first color when the determined tool-to-bone offset is less than the first level magnitude; displaying the determined tool-to-bone offset in a second color, different from the first color, when the determined tool-to-bone offset is between the first level and the second level magnitude; and displaying the determined tool-to-bone offset in a third color, different from the first and the second colors, when the determined tool-to-bone offset is greater than the second level magnitude.

12. The method of claim 11, further comprising defining a third level magnitude, and disabling power from the controller to the surgical instrument when the determined tool-to-bone offset is greater than the third level magnitude.

13. The method of claim 5, further comprising prompting a user to enter a value for the predefined magnitude.

14. The method of claim 5, wherein triggering an action comprises prompting a user to update a model of the bone, and wherein updating the model of the bone comprises contacting a resected surface of the bone with the instrument tool tip while power is disabled from the controller to the surgical instrument.

15. A method of operating a surgical system during a surgical operation to verify a tracking registration, the surgical system including a navigation system including a localizer having a localizer coordinate system, an instrument tracker coupled to a surgical instrument, the surgical instrument including a tool tip, a patient tracker coupled to a patient's anatomy, and a control console in communication with the localizer, the control console in communication with data representing the surgical instrument and data representing the patient's anatomy, the method comprising:
 tracking, with the navigation system, the surgical instrument and the anatomy and storing, with the control console, first data representing the tracked surgical instrument and second data representing the tracked anatomy in a common coordinate system;
 determining the tool tip is within a predefined proximity to the tracked anatomy based on the first data representing the tracked surgical instrument and second data representing the tracked anatomy;
 determining the tool tip does not depart the predefined proximity by more than a predefined magnitude over a predefined duration;
 determining an offset distance based on the first data representing the tracked surgical instrument and the second data representing the tracked anatomy;
 comparing the offset distance to a predefined threshold; and
 triggering an action when the offset distance is greater than the predefined threshold.

16. The method of claim 15, further comprising prompting a user to verify a tracking registration by one of displaying a prompt on a display; sounding an audible alert; generating a haptic sensation; or combinations thereof.

17. The method of claim 15, wherein determining the tool tip is within a predefined proximity to the tracked anatomy includes defining a surface area of the anatomy not to be resected, and determining the tool tip is within a predefined proximity to the defined surface area.

18. The method of claim 15, wherein the offset distance is defined as a magnitude of minimum separation between the tool tip and the tracked anatomy in the common coordinate system, or as a magnitude of greatest overlap between the tool tip and the tracked anatomy in the common coordinate system.

19. The method of claim 15, wherein determining the tool tip is within a predefined proximity to the tracked anatomy includes the surgical instrument positioned at a first pose with respect to the tracked anatomy, the surgical instrument defining a first proximal point of the tool tip and wherein determining the offset distance includes determining a first offset distance;
 the method further comprising determining the tool tip is within a predefined proximity to the tracked anatomy including the surgical instrument positioned at a second pose with respect to the tracked anatomy, the surgical instrument defining a second proximal point of the tool tip and wherein determining the offset distance includes determining a second offset distance; and wherein comparing the offset distance to a predefined threshold includes comparing the first offset distance to the predefined threshold, and comparing the second offset distance to the predefined threshold, and wherein triggering an action includes initiating an action when the first offset distance, the second offset distance, or both the first and second offset distances are greater than the predefined threshold.

20. The method of claim 19, wherein the surgical instrument includes an elongated aspect terminating at the tool tip, the elongated aspect defining a longitudinal axis extending substantially parallel to the elongated aspect; and wherein the second proximal point is at least 90° from the first proximal point relative to a rotation about the longitudinal axis.

21. The method of claim 19, wherein the surgical instrument includes the tool tip having a spherical aspect defining a centerpoint, wherein the second proximal point is at least 90° away from the first proximal point relative to a rotation about the centerpoint.

22. The method of claim 15, wherein triggering an action includes one of sounding an audible alert, displaying a visual alert, activating a tactile alert, cutting off power to the surgical instrument or combinations thereof.

23. The method of claim 15, wherein the predefined threshold includes a first predefined threshold, and a second predefined threshold, and wherein triggering an action includes triggering a first action when the offset distance is greater than the first predefined threshold but less than the second predefined threshold, and triggering a second action when the offset distance is greater than the second predefined threshold, wherein the first action includes one of sounding a first audible alert, displaying a first visual alert, activating a first tactile alert or combinations thereof, and wherein the second action includes one of sounding a second audible alert, displaying a second visual alert, activating a second tactile alert or combinations thereof.

24. A method of providing navigation guidance for a surgical procedure using a navigation system, the navigation system comprising a localizer, the method comprising:

registering a patient's anatomy in a common coordinate system, the patient's anatomy including at least a first bone and a second bone;

registering a surgical instrument in the common coordinate system, the surgical instrument comprising a tool tip;

tracking the patient's anatomy and the surgical instrument with the navigation system during operation of the surgical instrument on the first bone of the patient's anatomy;

determining the tool tip is within a predefined proximity to the second bone;

determining the tool tip does not depart the predefined proximity by more than a predefined magnitude over a predefined duration;

determining an offset distance based on the tracked position of the surgical instrument and the second bone;

comparing the offset distance to a predefined threshold;

triggering an action when the offset distance is greater than the predefined threshold; and tracking the patient's anatomy and the surgical instrument with the navigation system during operation of the surgical instrument on the second bone of the patient's anatomy.

\* \* \* \* \*